US009795460B2

(12) United States Patent
Martz et al.

(10) Patent No.: US 9,795,460 B2
(45) Date of Patent: Oct. 24, 2017

(54) TOOTH-POSITIONING APPLIANCE FOR CLOSING SPACES

(71) Applicants: Martin G. Martz, Bakersfield, CA (US); Andrew S. Martz, Bakersfield, CA (US)

(72) Inventors: Martin G. Martz, Bakersfield, CA (US); Andrew S. Martz, Bakersfield, CA (US)

(*) Notice: Subject to any disclaimer, the term of this patent is extended or adjusted under 35 U.S.C. 154(b) by 20 days.

(21) Appl. No.: 14/645,622

(22) Filed: Mar. 12, 2015

(65) Prior Publication Data

US 2015/0257856 A1    Sep. 17, 2015

Related U.S. Application Data

(60) Provisional application No. 61/952,364, filed on Mar. 13, 2014.

(51) Int. Cl.
| | | |
|---|---|---|
| *A61C 3/00* | (2006.01) | |
| *A61C 7/08* | (2006.01) | |
| *A61C 7/14* | (2006.01) | |
| *A61C 7/00* | (2006.01) | |

(52) U.S. Cl.
CPC ............... *A61C 7/08* (2013.01); *A61C 7/002* (2013.01); *A61C 7/14* (2013.01); *A61C 7/145* (2013.01)

(58) Field of Classification Search
USPC ...................................................... 433/6, 20
See application file for complete search history.

(56) References Cited

U.S. PATENT DOCUMENTS

| | | | |
|---|---|---|---|
| 3,218,714 | A | 11/1965 | Wallshein |
| 3,302,288 | A | 2/1967 | Tepper |
| 3,477,129 | A | 11/1969 | Rubin |
| 3,486,231 | A | 12/1969 | Nelson |
| 3,526,961 | A | 9/1970 | Kesling |
| 3,916,526 | A | 11/1975 | Schudy |
| 4,184,254 | A | 1/1980 | Kraus |
| 4,284,405 | A | 8/1981 | Dellinger |
| 5,013,239 | A | 5/1991 | Kesling |
| 5,727,941 | A | 3/1998 | Kesling |
| 6,217,323 | B1 | 4/2001 | Liou |

(Continued)

OTHER PUBLICATIONS

International Search Report and Written Opinion for Application No. PCT/US16/22024 mailed May 26, 2016.

*Primary Examiner* — Nicole F Johnson
*Assistant Examiner* — Nicole F. Lavert
(74) *Attorney, Agent, or Firm* — Brake Hughes Bellermann LLP

(57) ABSTRACT

A tooth-positioning appliance for closing spaces has at least two appliance segments, each segment having a thin elastomeric shell with recesses for removably engaging a set of teeth, and tooth-clasping elements for removably engaging bonded attachments protruding from the teeth. One of the appliance segments includes a flat receptacle extending horizontally on the thin shell of the appliance segment, and the other appliance segment has a thin elongated tab extending laterally from the second appliance segment spanning the space to be closed, and in sliding engagement with the flat receptacle of the other appliance segment. An activating element is connected between the appliance segments to exert a force to change the size of the space between the sets of teeth as the tab slides with respect to the flat receptacle.

16 Claims, 20 Drawing Sheets

(56) References Cited

U.S. PATENT DOCUMENTS

| | | | | |
|---|---|---|---|---|
| 6,572,372 B1* | 6/2003 | Phan | ............ | A61C 7/00 |
| | | | | 433/18 |
| 8,356,993 B1 | 1/2013 | Marston | | |
| 8,517,726 B2 | 8/2013 | Kakavand et al. | | |
| 2010/0227289 A1* | 9/2010 | Farrell | ............ | A61C 7/08 |
| | | | | 433/6 |
| 2010/0279245 A1 | 11/2010 | Navarro | | |
| 2011/0136072 A1* | 6/2011 | Li | ............ | A61C 7/08 |
| | | | | 433/18 |
| 2011/0311937 A1* | 12/2011 | McCance | ............ | A61C 7/00 |
| | | | | 433/20 |
| 2012/0129117 A1* | 5/2012 | McCance | ............ | A61C 7/10 |
| | | | | 433/7 |
| 2013/0309624 A1* | 11/2013 | Smith | ............ | A61C 7/285 |
| | | | | 433/9 |

* cited by examiner

TOOTH-POSITIONING APPLIANCE FOR CLOSING SPACES

RELATED APPLICATION

The present application is based on and claims priority to the Applicants' U.S. Provisional Patent Application 61/952,364, entitled "Tooth-Positioning Appliance For Closing Spaces," filed on Mar. 13, 2014.

BACKGROUND OF THE INVENTION

Field of the Invention

The present invention relates generally to the field of orthodontics. More specifically, the present invention discloses a tooth-positioning appliance for closing a space between teeth.

Statement of the Problem

A wide variety of orthodontic aligners have been used for many years in repositioning teeth during orthodontic treatment. It should be noted that the terms "aligner", "positioner" and "tooth-positioning appliance" are largely synonymous as used in the orthodontic field.

This type of orthodontic treatment typically involves separate tooth-positioning appliances for the upper and lower teeth. The tooth-positioning appliances fit over the teeth, covering nearly all of the facial and lingual surfaces, and also most of the occlusal, or biting surfaces of the teeth. The early positioners described in the prior art were made from a set of plaster models derived from three-dimensional negative dental impressions of the patient's teeth. The plaster dental models were modified by cutting the teeth apart using a small jeweler's saw or rotary cutting discs and repositioning the plaster teeth in a better, straighter, desired arrangement, and holding the teeth in the new arrangement by using dental wax. The reset teeth molds provide the basis for manufacturing the positioners. The resilience of the material from which the positioner is made provides the energy to move the teeth from their original position toward the new straightened position. From the earliest disclosure of the tooth positioner, many of the proposed designs in the prior art have shown moving the teeth in a series of incremental steps. Making a series of appliances is difficult if the tooth arrangement for each step must be made by hand using plaster and wax.

Starting in the early 1990's, digital technologies have begun to provide orthodontists with fundamentally new tools for delivering orthodontic treatment by fabricating tooth models in small but accurate incremental steps. Commercially-available CAD/CAM (computer-aided design and manufacturing) software can produce the desired tooth models, from which a progressive series of appliances can be manufactured. These tools include 3D imaging of the patient's dentition, and CAD/CAM systems for creating virtual models in orthodontic treatment to then produce customized orthodontic appliances.

An example of the successful orthodontic application of these digital technologies is seen in the commercial service known as the Invisalign® program by Align Technology, Inc. of San Jose, Calif. The Invisalign program is largely based on U.S. Pat. No. 5,975,893 (Chishti et al.) and many related patents, including U.S. Pat. No. 6,398,548 (Muhammad et al.). Invisalign tooth positioners are a progressive series of thin, transparent, U-shaped plastic appliances formed over computer-generated forming patterns grown from a virtual model of the patient's dental anatomy. The process for forming aligners uses a combination of vacuum, pressure and heat. This forming process is informally referred to within the orthodontic laboratory community as the "suck down" process.

In order to produce a series of Invisalign-type tooth aligners, a technician first scans a patient's upper and lower model set to obtain CAD-manipulatable virtual models of a patient's dental anatomy. Alternative methods for obtaining a 3-D virtual image of a patient's dental anatomy include: (1) using an industrial C-T machine to directly scan a negative 3-D impression made from a stable silicone rubber or polyvinyl siloxane material without pouring up a plaster model (the method currently favored by Invisalign) or (2) directly light-scanning a negative impression made from any material of the patient's teeth; or (3) directly scanning the patient's teeth with an intra-oral scanner. All of these methods are currently available and widely used. A model set normally consists of one upper and one lower plaster model of the teeth, palate and gums. Once the virtual model of the original malocclusion has been obtained, a technician will then undertake steps involving extensive manipulation of the virtual malocclusion. This involves extensive repositioning of the teeth according to a comprehensive and sequential procedure, ultimately arriving at a finished or ideal occlusion for that patient. The finished occlusion in the virtual model is consistent with the complete repositioning of the patient's upper and lower occlusion that would result at the end of successful conventional orthodontic treatment.

After the steps described above are accomplished, the technician possesses two versions of the patient's teeth available within the virtual CAD environment. One version represents the original malocclusion and the other represents the ideal occlusion. In other words, the technician has the beginning and the end states.

The next step in the Invisalign process involves the creation of an incremental, progressive series of physical forming models. Each of these forming models represents a snapshot of the patient's future occlusion at specific incremental steps along the patient's proposed treatment sequence between the beginning and the end conditions as described above. To accomplish this, the technician creates a virtual "first transition model" that sees a slight repositioning of all or most of the teeth. This first transition model sees some or all of the teeth being subtly moved from their original pre-treatment positions to a virtual first transition position that is in the direction of their intended finished positions. Similarly, a second virtual transition model is created that sees the virtual teeth being moved again slightly further in the desired directions. The objective of the Invisalign technician is to create a series of progressive models, each biased slightly further than the previous one, and each moving the teeth slightly closer to their finished target positions. A final forming model will take the teeth from the series of transition positions and move them into their final, desired positions.

Once such a series of virtual intermediate forming models has been created and a final forming model has been created by the Invisalign technician, the digital code representing each of the models in the series is directed to operate a computer numerically-controlled (CNC) machine known as a rapid prototyping machine. Within a rapid prototyping machine, the series of physical forming models are grown using any of number of conventional processes, such as stereo lithography or 3D printing. The growing step results in the production of hard, physical duplicates of each of the series of virtual intermediate models and the final model.

The next step of the Invisalign process sees each of the series of physical models being in turn mounted in a suck-down machine where a combination of pressure, heat and vacuum is used to form the actual series of progressive aligners from plastic sheet material of a constant thickness. Once the series of progressive aligners are formed and trimmed, they are sequentially labeled, packaged and shipped to the attending orthodontist. The orthodontist then schedules an appointment for the patient, at which time the aligners and instructions for their use are given to the patient. The patient is instructed to wear the first set of aligners for a period of time, typically two weeks. After that, the first set is discarded and the patient transitions to the next set of the series and so on.

The aligners serve to urge the patient's teeth to move according to the positional biases created virtually by the Invisalign technician. The teeth are progressively biased and urged to move in desired directions toward their predetermined finished positions by the resilience of the polymeric material of the aligner. In response to the forces delivered by the aligners, certain physiological processes involving the creation and resorbtion of the bone supporting the roots of the teeth are initiated. The net result is the slow, progressive orthodontic movement of the roots of the teeth through the underlying bone toward desirable positions and orientations.

Progressive thin-shell aligners have proven to be very effective in treating some types of orthodontic cases, but they have shortcomings in other situations. In particular, a significant percentage of orthodontic treatments require tooth extractions for various reasons, such as severe crowding of the patient's teeth. Percentages are reported to range from 25% to 50% in some practices.

When severe dental crowding is present, the teeth most often removed to create space are the first premolars. Orthodontists do not like removing anterior teeth (cuspids or incisors) primarily because they are highly visible, but even after all extraction spaces are closed, it is often obvious if an anterior tooth is missing unless the teeth can be reshaped. The front teeth have a distinctive appearance and other teeth substituted in their place often don't quite fit there. On the other hand, removal of large molar teeth presents difficulties with space closure and usually the crowding is in the front part of the mouth. Removing two or four premolars (the teeth in the middle of each side) allows a satisfactory appearance and is more easily accomplished. Occasionally, for various reasons, orthodontists may still find it necessary to remove either anterior teeth or molars, and occasionally these teeth are already missing prior to orthodontic treatment.

Closing significant spaces in orthodontics presents a challenge, whether the spaces were produced by extracting teeth as part of the orthodontic treatment plan, or whether the spaces were present prior to treatment.

Orthodontists usually want to completely close extraction sites by moving the teeth on either side of the extraction site together, and it is desired to have parallel roots on all of the teeth after the extraction sites have been closed. With conventional aligners, as the teeth adjacent to the extraction site are moved, the crowns of the teeth tend to tip toward each other, and the roots, where the greatest resistance to movement is encountered, tend to trail behind. The problem is caused primarily by poor engagement of the aligner on teeth that are adjacent to tooth extraction sites. The other teeth, farther away from the extraction sites also tend to tip as well, again because the aligner does not engage the teeth very well. In other words, the roots fail to move as much as the crowns of the teeth move. Therefore, a need exists for a removable orthodontic appliance that can be used during the space-closure stage of treatment without tipping adjacent teeth into the extraction sites.

Solution to the Problem

The present invention addresses this shortcoming in the prior art by providing a removable appliance for use in the space-closure stage of orthodontic treatment. It is capable of closing spaces without tipping teeth with a similar degree of control to that achieved with fixed braces. In particular, the present appliance is divided into anterior and posterior appliance segments on groups of teeth on either side of the extraction sites. Each appliance segment removably engages a selected set of teeth aided by attachments bonded to the teeth. Elongated, thin elastomeric tabs extend laterally from selected appliance segments to span the extraction sites and slide in corresponding flat receptacles (e.g., tubes or molded plastic receptacles) specially shaped to receive the tabs on other appliance segments. These elastomeric tabs allow relative anterior-posterior movement of the appliance segments and their associated groups of teeth to close the extraction sites. The flat shape of the tabs and slots, and the strength of the appliance segments result in an assembly that is fairly rigid in a vertical plane. This provides improved leverage to keep teeth in an upright position and to prevent the tipping of adjacent teeth into the extraction sites.

SUMMARY OF THE INVENTION

This invention provides a thin-shell tooth-positioning appliance for closing a space between a patient's teeth. The appliance is divided into a plurality of segments removably attached to groups of teeth on opposing sides of the space to be closed. Each appliance segment removably engages selected teeth aided by attachments bonded to the teeth. Elongated, thin elastomeric tabs extend laterally from selected appliance segments to span the space and slide in corresponding flat receptacles on other appliance segments. A tractive element, such as an elastic band or spring device, can be connected between the appliance segments to slowly close the space as the tabs slide with respect to the receptacles. Optionally, a pushing element could be utilized in place of the tractive element to open space or increase the size of an existing space.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
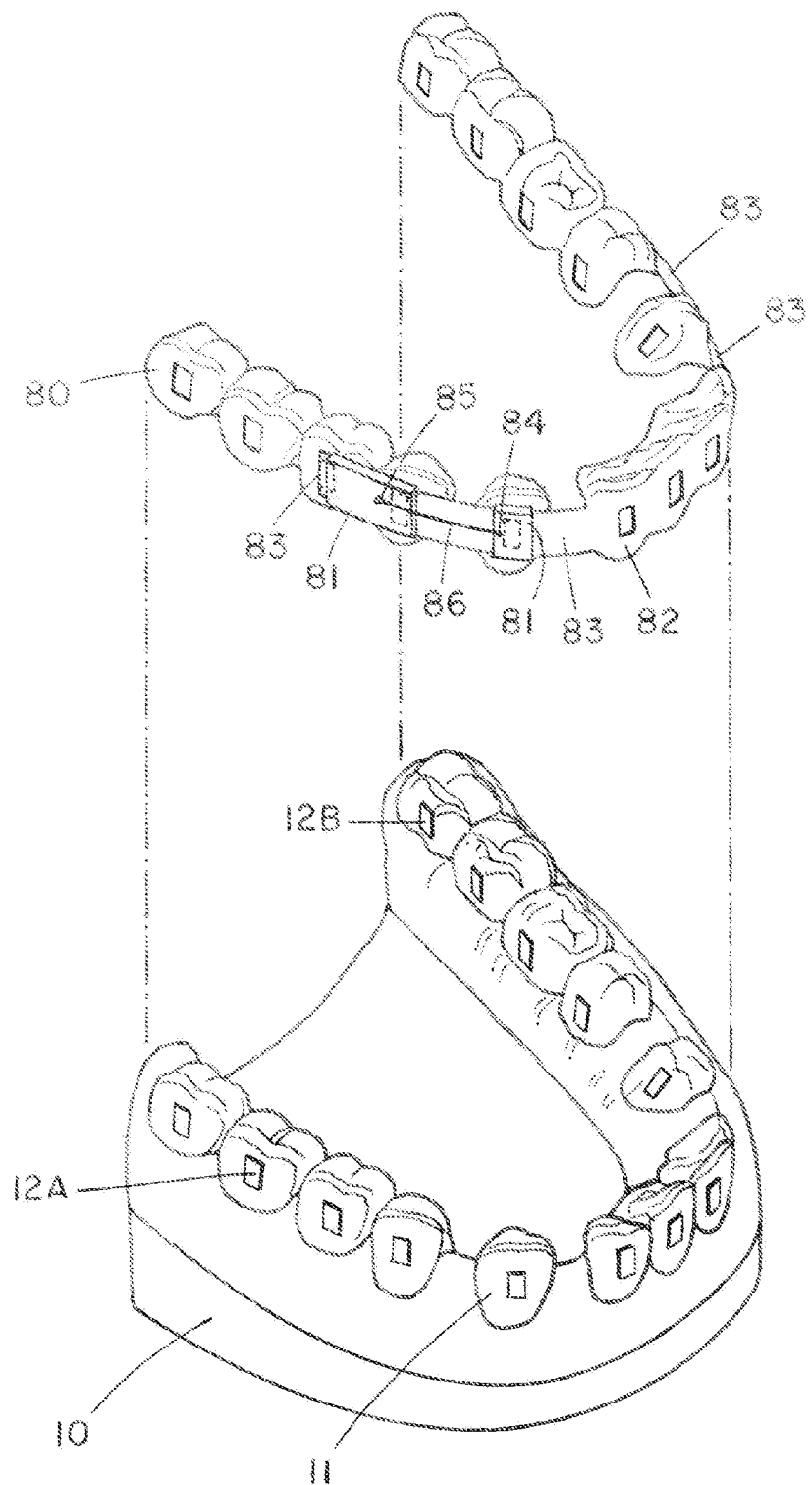
FIG. 1 is a perspective view of an embodiment of the present appliance, including a patient's lower teeth from which the two lower first premolars have been extracted.

Turning to FIG. 1, the present tooth-positioning appliance includes the following major elements: (1) bonded attachments 12A, 12B bonded to the lingual or buccal surfaces of selected teeth 11; (2) a plurality of thin-shell appliance segments 80, 82 on opposing sides of the space to be closed that removably engage the bonded attachments 12A, 12B on selected groups of teeth; (3) thin elongated tabs 83 extending laterally from selected appliance segments to span the space and slide in corresponding flat horizontal receptacles 81 (e.g., flat tubes or molded plastic receptacles) on the lingual and/or buccal aspects of other appliance segments; and (4) tractive elements 86 connected between the appliance segments to slowly close the space as the tabs 83 slide with respect to the receptacles 81. Optionally, a pushing element could be utilized in place of the tractive element to open space or increase the size of an existing space. More generally, either a tractive element or a pushing element can be considered as an "activating element" to change a space as the tabs 83 slide with respect to the receptacles 81.

The bonded attachments 12A, 12B are typically projecting elements or buttons that have been bonded to the buccal or lingual surfaces of selected teeth 11, as shown in FIG. 1. The bonded attachments 12A, 12B and are not typically removable by the patient during the course of active orthodontic treatment. For example, the bonded attachments 12A, 12B can have a substantially rectangular shape with parallel sides, although it is to be understood that there are many possible shapes for bonded attachments that would be suitable. The bonded attachments 12A, 12B are utilized for two purposes: (1) the bonded attachments 12A, 12B increase the retention of the appliance segments 80, 82 to the teeth 11, (or in other words, the appliance segments are less likely to become dislodged from the desired location on the teeth); and (2) the bonded attachments 12A, 12B have a shape that allows the appliance segments 80, 82 to effectively clasp the teeth, and transmit desired forces to the teeth in three-dimensions, thereby providing control over root movement. In the rectangular bonded attachment 12A, 12B shown in FIG. 1, the parallel outer edges of the bonded attachment 12A, 12B provide surfaces for positive engagement to allow forces to be applied to the teeth to accomplish root movement under control. Inner surfaces of an attached projection such as can be provided by grooves or special shapes can also provide this control. Grooves or special outside shaping can help guide the appliance segments 80, 82 into position. The bonded attachments can be pre-made of any suitable material including dental composite, clear or tooth-colored ceramic materials, or any suitable clear plastic material. The attachments 12A, 12B can be bonded to the teeth using conventional bonding techniques and adhesives that are well-known in the art including the steps of mildly acid-etching the enamel prior to bracket placement. A technique well known in the art called indirect bonding can be utilized, with a pre-formed guide made of flexible material holding the attachments in the desired position while the adhesive is curing to ensure accurate attachment placement on the teeth. The bonded attachments can alternatively be fabricated out of dental composite using pre-made hand-held molds for one tooth at a time placement, commercially available for this purpose. A third alternative is to utilize a mold made using 3D CAD/CAM technology, where the shape and the size of the bonded attachments are planned in the computer and a model of the entire dental arch with attachments in place is printed using a 3-D printer. From this model, a mold is made from which to fabricate and place dental composite attachments in precisely the right location directly on the teeth. Alternatively, the mold for precisely placing the bonded attachments made of dental composite can be printed directly.

The appliance segments 80, 82 can be made of a thin elastomeric material having a number of recesses for removably receiving and clasping a predetermined set of teeth. For example, the embodiment depicted in FIG. 1 has an anterior appliance segment 82 for removably engaging the patient's anterior lower teeth, and two posterior appliance segments 80 for removably engaging the posterior lower teeth. The posterior appliance segments 80 are separated from the anterior appliance segment 82 by two spaces to be closed, which are typical first premolar extraction sites.

Preferably, the appliance segments 80, 82 include a number of holes of precise dimensions (e.g., rectangular holes) through which the bonded attachments 12A, 12B project to removably engage the appliance segments 80, 82. Alternatively, a recess on the inside of the appliance segment of the same shape and size as the bonded attachment 12A, 12B should work equally as well, particularly if the appliance segment is printed, because of the ability of the printing process to produce a more precise fit than can be obtained by thermoforming.

It should be noted that the appliance segments can be designed to engage a plurality of adjacent teeth, as shown in FIG. 1. For example, a plurality of posterior teeth can serve as a fixed anchorage for moving anterior teeth, or in some cases, it is desirable to move a plurality of anterior teeth as a group. However, an appliance segment could be designed to engage a single tooth, if necessary. In this case, the appliance segment can be a single tooth-clasping element with a suitable holes or recesses for removably engaging the bonded attachments on a tooth.

The appliance segments 82 are connected by interconnecting elements in the form of thin, elongated elastomeric tabs 83 that extend laterally from selected appliance segments to span the space to be closed, and slide in corresponding flat receptacles or slots 81 on other appliance segments 80. The tabs 83 are relatively flat in the vertical plane to provide a significant degree of stiffness to help maintain horizontal alignment of the teeth during treatment. However, the tabs 83 can freely slide in the anterior-posterior directions with respect to the receptacles 81. In addition, the tabs 83 are relatively flexible in the lingual/labial directions. In some embodiments of the present invention, the appliance segments are initially made of one piece of material, and the flat tabs are all part of a monolithic whole unit. Functionally, different regions of a single-piece positioner can serve as the appliance segments 80, 82 and sliding tabs 83.

A tractive element (e.g., an elastic 86 or an open coil spring along an associated spring guide) can be connected between hooks or buttons 84, 85 on the appliance segments 80, 82 to slowly close the space as the tabs 83 slide with respect to the slots 81. We could also open space by using a pushing element, such as a flexed element (e.g., a smaller version of a Jasper Jumper).

The present tooth-positioning appliance can be fabricated using any of a variety of manufacturing techniques. For example, it can be produced by planning and designing the appliances using computerized 3-D CAD/CAM software. Many off-the-shelf software programs are currently available that are capable of this function. Over the long-term, it will be beneficial to write new software that integrates easily with the skill levels of orthodontist end-users, to simplify their use of the product. Open-source software that can be modified is currently available to perform this function. The standard surface-mapping computer algorithms define the surface as a series of triangles. The actual physical production of the appliances can be accomplished by vacuum-forming thermoplastic materials over models produced digitally and combining the thermoformed portion of the appliance with the other necessary elements. This step is followed by using computer automated trimming technologies such as CNC milling or laser cutting. In particular, the clear appliance segments could be produced by vacuum thermoforming a clear plastic material for improved aesthetics.

Alternatively, positioners can be made without first producing 3D models via 3D printing. A big advantage of direct 3D printing is that more complex shapes could be more easily printed, and almost no trimming of excess material would be necessary, saving time and avoiding wasted material. Some new 3D printers can print more than one material at the same time. The flexible sliding tabs 83 could be printed along with the appliance segments 80, 82, and they could be made of differing materials. The materials can be blended or intertwined which will avoid the need for a separate attachment step in manufacturing. Another option involves direct CNC milling of the appliance segments or other portions of the appliances from a block of plastic material.

In terms of treatment methodology using the present appliance, all of the posterior teeth in each arch, upper and lower, will typically be tied together in a unit as rigid as possible to form an appliance segment involving ideally at least six teeth per arch, with three teeth on each side. In some circumstances, particularly where teeth are missing, fewer anchor teeth may be available. It will be advantageous to connect the teeth on the right and left sides together. In the upper arch, this can be accomplished using a palatal bar, or at the very least a thin shell of plastic material covering the palate, in much the same way as a conventional acrylic retainer covers the palate. Alternatively, a printed plastic palatal bar, possibly with reinforcing ribs or ridges could be utilized. In the lower arch, it may be necessary to use a heavy wire lingual arch going behind the front teeth. Alternatively, a metal lingual bar or a molded plastic or printed plastic lingual connector, possibly with reinforcing ribs or ridges could be used to connect the teeth on both sides together.

On the buccal surface of the posterior appliance segment on each side, a large vertically-oriented plastic rectangular receptacle can be placed to receive a tab, or band of clear material attached to the cuspid teeth on either side. The tab attached to the cuspid will slide through the rectangular receptacle. An elastic band of a suitable material can be attached to a hook on the posterior segment and, at the other end, a hook can be attached to the appliance segments fitted on the cuspid tooth on each side. The elastic band supplies a force to slowly bring the cuspid tooth posteriorly (toward the back of the mouth). The clear plastic tab on the cuspid just fits precisely into the rectangular receptacle on the posterior appliance segment, allowing the tab to slide freely into the receptacle, and at the same time it keeps the cuspid tooth upright and prevents the crown from tipping distally as the entire cuspid tooth moves slowly back into the extraction site. The front teeth can be left alone during the first few months of the cuspid retraction. If they are crowded they will start to drift distally and usually will become straighter as space is made available for them. If there is excessive space in the anterior region, an anterior appliance segment can be added to begin straightening the incisors.

For example, the anterior appliance segment may have a tab extending back through an additional appliance segment placed on the cuspid, that now has attached a similar large rectangular receptacle similar to the one already in place on the posterior appliance segment. The long tab on the anterior segment can extend all the way from the anterior segment, through the receptacle on the cuspid segment, and through the receptacle on the posterior segment. The tab keeps the anterior segment stabilized while the anterior teeth are becoming aligned. There may be several stages of the anterior segment, each one slightly different from its predecessor stage, toward an intermediate goal of having nicely aligned incisor teeth. While the anterior teeth are becoming aligned, retraction of the cuspid into the extraction space will continue with elastics being utilized to provide the force for continued cuspid retraction. The cuspid is free to slide along the tab extending from the anterior segment to the posterior segment.

Depending on the treatment philosophy, and the malocclusion problem, some orthodontists may want to apply a second elastic band on each side to also retract the incisor teeth at the same time the cuspids are being retracted. Of course, the orthodontist will have to pay attention to the relationship between the upper and lower teeth while the extraction spaces are becoming closed. The treatment plan and the simulated movements in the computer will help to make sure the movement of the teeth is progressing according to plan. Some use of inter-arch elastics (as are routinely used with fixed braces) will help to keep the plan progressing as it should. Another option is to use fixed temporary anchorage devices (TAD's), essentially temporarily placed metal threaded screws which are placed through the dental epithelium into the supporting alveolar bone tissue. From these metal screws used as hooks, elastic bands can be installed to attach to the removable appliance segments to apply desired traction forces to enhance tooth movement. This technique is widely used by orthodontist with fixed braces. The more difficult nature of extraction cases makes it more likely that some remedial treatment planning will be necessary to keep the tooth movement progressing in a satisfactory manner. Predicting actual tooth movement paths with 100% accuracy for an extraction case is likely too difficult for the typical orthodontist. It may be necessary to take new impressions or a new intra-oral scan to make an accurate new digital data set to correspond to an intermediate position to make the new appliances for finishing the case. After the spaces are closed, additional positioner stages may be necessary to finish the case in a similar manner to the continued orthodontic treatment that is usually needed after space closure when braces are used.

Returning to FIG. 1 in more detail, this drawing shows a perspective view of a dental model 10 of a set of lower teeth 11. The two lower first premolars have been extracted. The four lower incisors are grouped together in the anterior region. The posterior teeth, including the two second premolars are grouped together on each side. At this stage of treatment, the cuspid teeth have been partially retracted, and are approximately midway between the incisor group of teeth and the posterior teeth on each side. The upper portion of FIG. 1 shows a five-segment appliance positioned directly above the teeth, with vertical lines indicating how it is to be installed on the teeth below it. The first anterior appliance segment 82 fits over the incisors, including the sliding tabs 83 extending posteriorly that slide through flat receptacles 81 on the other appliance segments. The second and third appliance segments are the cuspid segments, which consist of individual tooth-clasping elements with their attached flat receptacles 81 having dimensions selected to precisely fit over the sliding tabs 83. The fourth and fifth appliance segments 80 fit over the posterior groups of teeth, left and right, with attached flat receptacles 81 to receive the sliding tabs 83 that extend from the anterior appliance segment 82.

Figure 7:
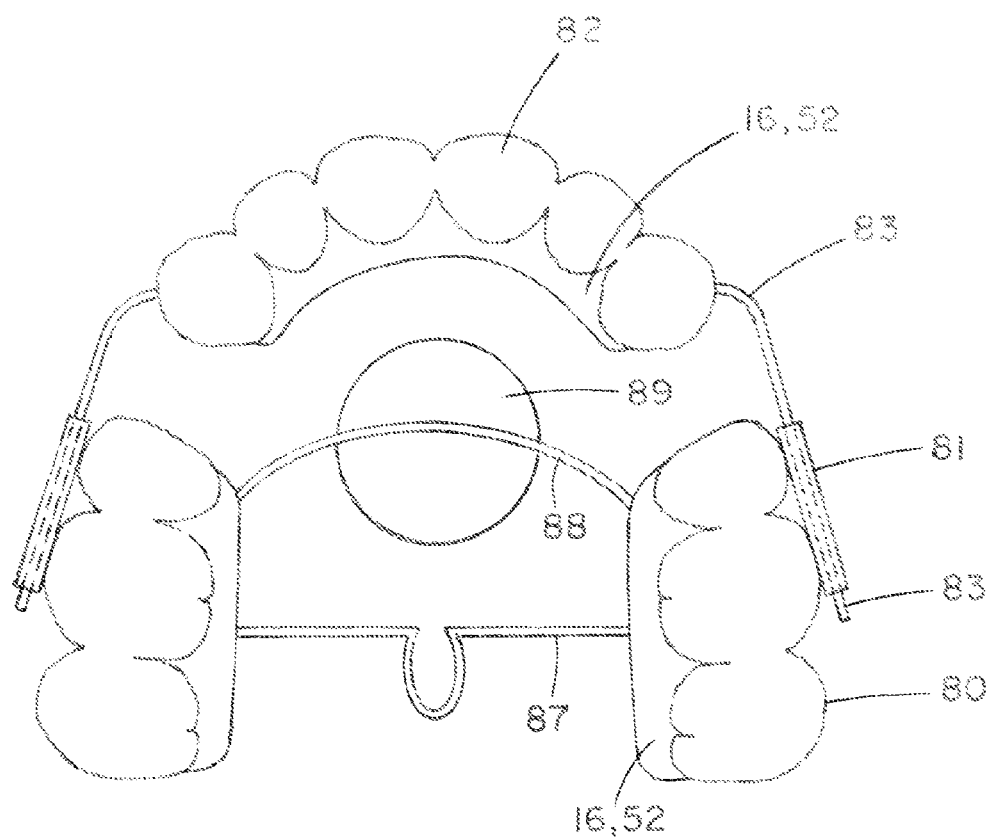
FIG. 7 illustrates an occlusal view of another appliance similar to that shown in FIG. 1, but includes a trans-palatal bar 87 and a palatal Nance holding arch 88 with its attached tissue-connecting pad 89.

The embodiment in FIG. 1 does not show any interconnection between the left and right posterior appliance segments 80. It is possible to make the appliance this way with separate left and right posterior appliance segments, but the appliance will be much more stable, and easier for the patient to use if the left and right posterior segments are attached to each other using some suitable means. For example, a heavy wire lingual arch, metal bar or plastic bar (possibly reinforced by ridges or ribs) can be utilized. If this same type of appliance is used in the upper arch, the left and right posterior segments can be attached to each other using some suitable means, such as a palatal bar, a Nance holding arch (as shown in FIG. 7), or with plastic palatal coverage as in a conventional Hawley retainer.

Figure 2:
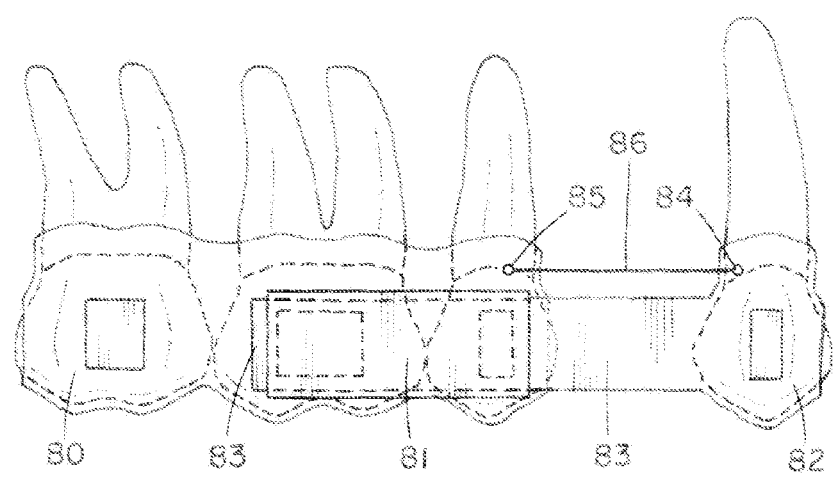
FIG. 2 shows a side view of teeth in the upper right quadrant with an attached appliance in place similar to the one shown in FIG. 1.

FIG. 2 shows a side view of teeth in the upper right quadrant with an attached appliance in place similar to the one shown in FIG. 1. This appliance is utilized for closing extraction spaces. Extraction cases are often treated with fixed braces in the early stages with a technique called "segmental retraction" and this removable appliance embodiment is designed to accomplish that purpose. The first premolar tooth has been extracted and the space is not closed. This appliance would be used at an earlier stage in treatment than the embodiment shown in FIG. 1. Two appliance segments are shown in this view. One appliance segment consists of an individual tooth-clasping element fitting over the cuspid tooth with an attached sliding tab 83 which extends posteriorly through the flat receptacle 81 on the posterior appliance segment 80. The posterior appliance segment 80 covers the second premolars, the first molars, and the second molars. A flat receptacle 81 is attached to the buccal side of the posterior segment 80. Since this is a right side view of the appliance, the teeth on the left side are not visible, because they are hidden from view by the structures on the right side. In actual use it would be very advantageous for this appliance to have the two posterior segments, left and right, connected together by some suitable means illustrated in other drawings in this disclosure. The posterior appliance segments will be much more stable as the cuspid teeth are retracted if the left and right posterior appliance segments are attached together. It will also be much easier for the patient to insert and remove the appliance if the left and right posterior appliance segments are attached together. Also, a second sliding tab could be utilized on each cuspid segment, along with an associated flat lingual receptacle on the posterior appliance segment. This embodiment, with buccal and lingual sliding tabs, is illustrated in an occlusal view in FIG. 8, which is discussed below.

Figure 3:
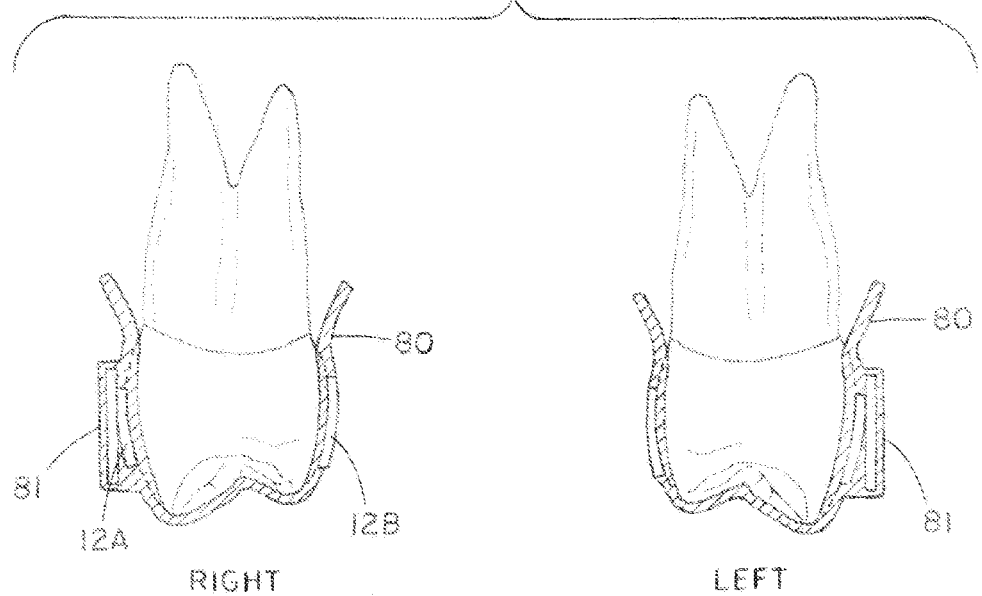
FIG. 3 shows an elevational view (as seen from an anterior position looking in a posterior direction) of the left and right posterior appliance segments shown in FIGS. 1 and 2 showing the appliance in place on a second premolar or molar tooth.

FIG. 3 shows an elevational view (as seen from an anterior position looking in a posterior direction) of the left and right posterior appliance segments 80 shown in FIGS. 1 and 2 with the appliance segments in place on a second premolar or molar tooth. The flat receptacle 81 to receive the sliding tab from the anterior appliance segment is shown on the buccal surfaces of the posterior appliance segments on both the left and right teeth.

The present appliance is typically made in at least two segments. The appliance segments on either side of the extraction sites have an excellent grip on a group of teeth. The sliding tabs (akin to collar stays) made of thin smooth plastic or other suitable material slide into flat rectangular receptacles with vertically-oriented openings sized to easily receive the tabs. The tabs slide smoothly into or through the receptacle, and the appliance segments engage multiple teeth on either side of the spaces to maintain the teeth in an upright position as the spaces are being closed. Elastic bands stretched between the appliance segments provide the force to bring the teeth together.

With the present appliance, we can consider placing a second tab-and-receptacle arrangement on the lingual side of the teeth as shown on the buccal side. In fact, in FIG. 2, the drawing would be exactly the same for both the buccal and lingual sides (i.e., a mirror image on the lingual side). Having two tabs would provide a second rotational moment on the teeth to cancel out the rotational moment applied by the appliance on the buccal (facial) side. This should prevent undesirable rotational tendencies on the teeth as the spaces are being closed, and it should not be significantly bulkier or much more difficult to make, particularly if the appliance is made using a 3-D printer.

In the embodiment shown in FIG. 2, the posterior appliance segment 80 covers all of the posterior teeth. In this case, there are two molars and one second premolar on each side behind the extraction space. Prior to extracting the teeth, depending on the treatment philosophy of the orthodontist, anchorage preparation typically includes the step of tipping the crowns of all the posterior teeth distally. The anchorage preparation may take a few stages to accomplish because molar teeth are large and are not likely to move easily. After anchorage preparation, the four first premolars will be removed, one in each quadrant.

Cuspid retraction is the next stage of treatment as illustrated in FIG. 2. There are three posterior teeth on each side in FIG. 2. All six posterior anchor teeth will be covered by a single-piece appliance segment to maintain their position. There are no individual tooth-clasping elements in the posterior region at this stage. The three teeth on the left side can be connected to the three teeth on the right side by a heavy lingual wire (e.g., a trans-palatal bar 87 as shown for example in FIG. 7, or some other suitable connecting means) to make each posterior appliance segment more stable. As previously discussed, a tab 83 is attached rigidly to the appliance segment 82 on the upper right cuspid. Preferably, this tab 83 is a flat ribbon-like piece of clear plastic that will serve as a guide for the movement of the isolated cuspid tooth (after extraction of the first premolar). For example, the tab 83 can be a flat vertical ribbon made of a flexible elastomeric material to allow a degree of flexibility in the horizontal plane, but provide rigidity in the vertical plane. The tab 83 slides through a vertically-oriented thin rectangular receptacle 81 with open anterior and posterior ends.

An elastic rubber band 86 is installed between two hooks 84 and 85 to supply a force to cause the cuspid to move distally. As part of the expected reaction force, all the posterior teeth contained within the single-piece posterior appliance segment will move mesially. The process of moving the cuspid will take several months. Typically, cuspids will move at a maximum rate of approximately 1 mm per month.

Figure 4:
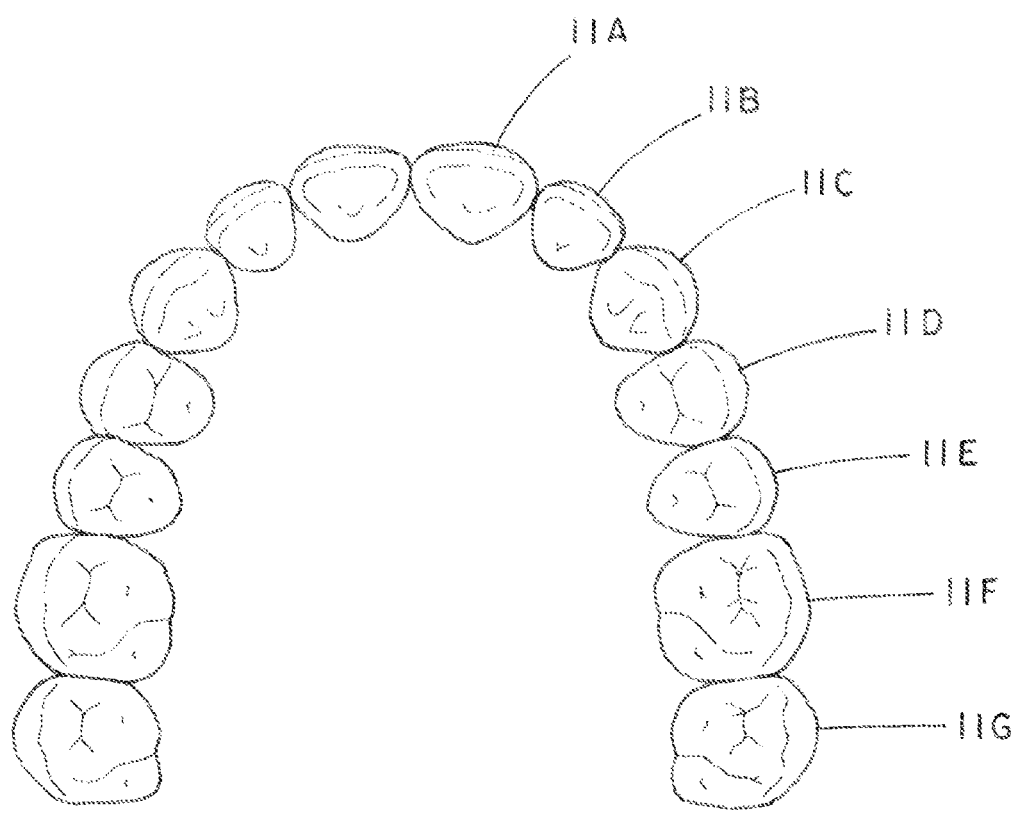
FIG. 4 shows an occlusal view of upper teeth.
Figure 5:
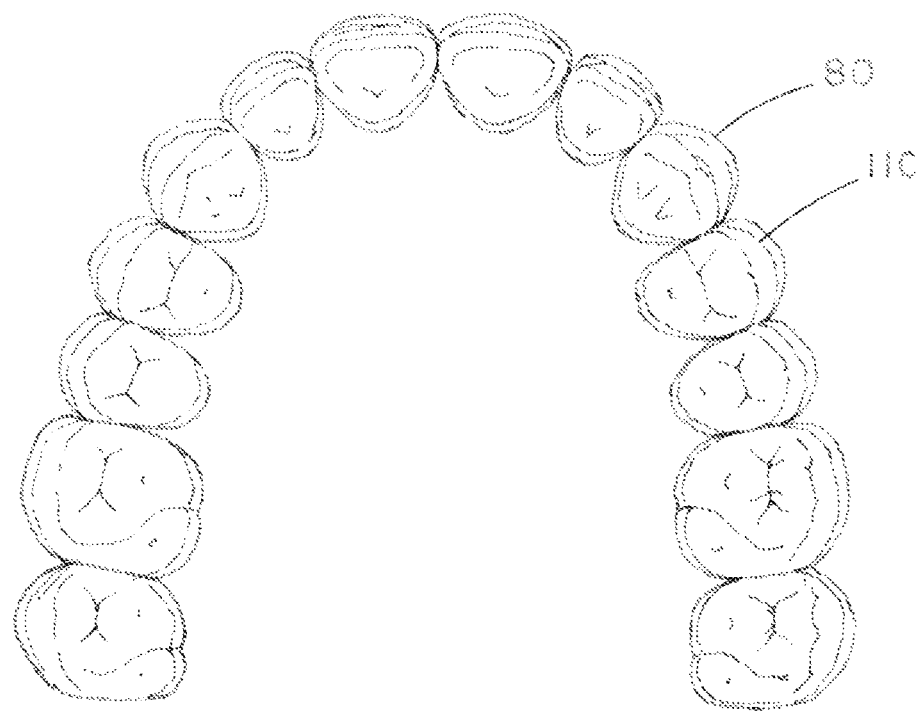
FIG. 5 is an occlusal view of the upper teeth shown in FIG. 4 with a clear aligner in place covering the teeth.
Figure 6:
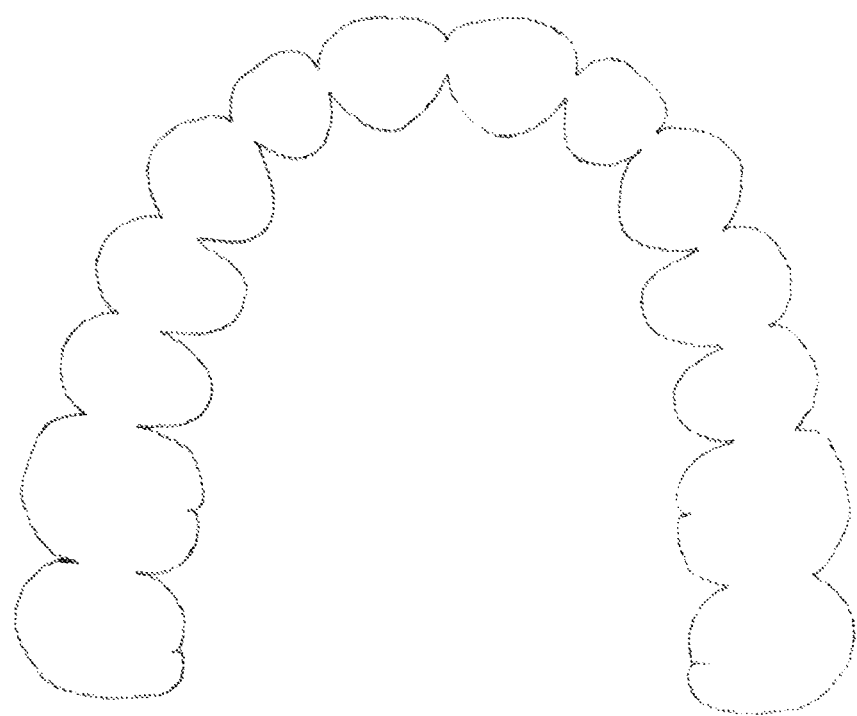
FIG. 6 shows an occlusal view of the appliance shown in FIG. 5 with the image of the underlying teeth removed, so the outline of the aligner is more easily visible.

FIG. 4 is an occlusal view of the upper teeth 11A-11G. FIG. 5 is an occlusal view of the same upper teeth shown in FIG. 4 with a clear aligner in place covering the teeth. In particular, there is a conventional thermoformed one-piece clear aligner in place wrapping around and covering the exposed surfaces of all the teeth. The buccal and lingual outlines of the teeth show a double line indicating the presence of the clear, thin aligner shell 80 around the outside peripheral outline of the teeth. FIG. 6 is an occlusal view of the same clear aligner shown in FIG. 5, with the image of the underlying teeth removed, so the outline of the aligner is more easily visible.

FIG. 7 is an occlusal view of an appliance similar to that shown in FIG. 1. This appliance is to be used primarily in the treatment of extraction cases. In this case, the first premolar teeth have been extracted. Some orthodontists prefer to retract the anterior group of teeth together in a single unit. The appliance is made in two segments that are detachable from each other when the appliance is removed from the mouth. The appliance has a posterior segment made up of the right and left tooth-clasping elements 80 with their associated lingual flanges 16, 52. The appliance segments are attached together across the posterior palate by a trans-palatal bar 87. Optionally, the appliance segments can be attached together by a Nance holding arch 88 in the anterior palate with its metal wire support bar and its plastic tissue-borne pad 89, or the two posterior segments can be attached by some other suitable means. Flat buccal tubes 81 receive the sliding tabs 83 that are attached to the anterior appliance segment 82. The anterior appliance segment in this particular embodiment consists of a single-piece appliance segment 82 covering all six anterior teeth with its associated lingual flange 16, 52. The sliding tabs 83 are integrally formed as part of the anterior appliance segment and extend posteriorly to insert in flat buccal tubes 81 on the posterior appliance segment. As shown in FIG. 1, elastic elements 86 can be hooked over the attachment hooks 84 and 85 to provide a force to achieve space closure after the tooth extractions.

The tooth-clasping elements of the appliance segments may include lingual flanges 16, 52. In this case, the anterior appliance segment is made up of a single tooth-clasping element with a single lingual flange covering a small area of gum tissue lingual to the group of anterior teeth. It is possible to also use a buccal anterior flange as well, but it is not visible in this occlusal view due to the angulation of the anterior teeth. In this embodiment, the right and left posterior appliance segments 80 cover the second molars, first molars, and second premolars. There is a lingual flange 16, 52 on the posterior appliance segments 80, left and right. Similarly, the anterior appliance segment 82 covering the six anterior teeth includes an associated lingual flange 16, 52.

A trans-palatal bar 87 connects the right and left posterior appliance segments across the posterior part of the palate. In this drawing, it is shown as it is commonly used in fixed orthodontic appliances as a metal wire with a midline omega-shaped adjustment loop. It is shown attached to the lingual flanges. The method of attachment can be any suitable method including embedding the metal wire in the plastic that forms the flange, attaching it with acrylic or thermoplastic material or by using composite dental adhesives. The bar does not have to be made of metal, but can be formed of thermoplastic material, or printed in a 3-D printer, or made of another suitable material. Optionally, it can have reinforcing ridges.

A Nance holding arch 88 is shown attached to the lingual flanges of the posterior appliance segments in much the same way as a trans-palatal bar 87. This is another optional way of attaching the posterior appliance segments together to provide control over arch width, to prevent or correct posterior tooth tipping and to better control posterior tooth anchorage during the space closing stages of extraction case treatment. It can be used simultaneously with or separately without a trans-palatal bar. The optional methods of attachment are basically the same as described earlier for the trans-palatal bar. The Nance holding arch 88 can also incorporate a plastic tissue-borne support pad 89.

Figure 8:
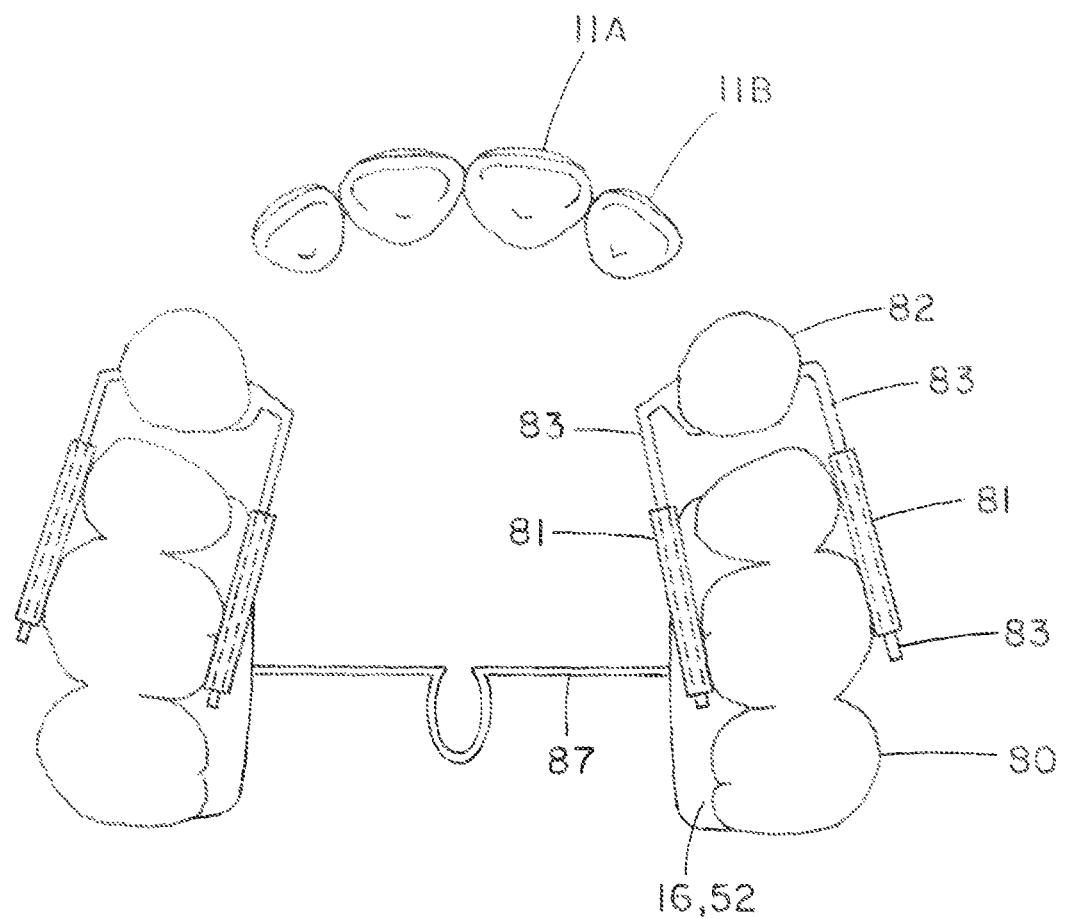
FIG. 8 presents an occlusal view of another embodiment of an appliance similar to that shown in FIG. 2, but includes a trans-palatal bar 87 and right and left tooth-clasping elements covering the cuspid teeth that have been partially retracted into the extraction spaces.

FIG. 8 is an occlusal view of another appliance similar to that shown in FIG. 2. The appliance is made in three segments that can be separated from each other for cleaning purposes when the appliance is removed from the mouth. It has a posterior segment with the left and right tooth-clasping elements 80 covering the second molars, first molars, and second premolars. There are associated lingual flanges 16, 52 that are part of the posterior tooth connecting elements. The right and left appliance segments can be connected together by a conventional trans-palatal bar made of metal wire with a central omega adjustment loop. The other two segments of the appliance are separate right and left tooth-clasping elements covering the cuspid teeth 82 with integrally formed sliding tab elements 83, designed to fit into rectangular receptacles 81 on the posterior appliance segment. Note that in this embodiment there are sliding tabs 83 on both the buccal and lingual sides of the upper cuspid tooth appliance segments and corresponding flat receptacles 81 on both the buccal and lingual sides of the posterior appliance segment. As shown in FIG. 2, elastic elements 86 can be hooked on over attachment hooks 84 and 85 to provide a force to achieve space closure after the tooth extractions. The parallel sliding tabs and receptacles with the parallel force application will allow the space closure to take place with a minimum of undesirable tooth tipping and rotation. As shown in FIGS. 1 and 2, bonded attachments on both the buccal and lingual sides of the teeth help to enhance appliance retention and provide three-dimensional control over tooth position.

The upper incisor teeth 11A, 11B etc. are left alone without any appliance coverage in this stage of treatment in this example. Generally, extraction treatment is utilized in the treatment of malocclusion cases with significant anterior crowding. More often than not, it is the anterior teeth that are crowded and overlapped, although in this drawing for the sake of simplicity, the incisor teeth are shown nicely aligned. In this stage of treatment, as the cuspid teeth are moved posteriorly to close the first premolar extraction spaces, the incisors can drift apart once the cuspids are out of the way, and alignment will be easier to accomplish when interdental spaces are present.

In this embodiment, the sliding tabs 83 are attached to and formed as an integral part of the two cuspid segments of the appliance. Note that there are a total of four sliding tabs 83 in this particular appliance, two on each side, left and right. The sliding tabs 83 insert into the four flat buccal and lingual tubes 81 on the posterior segment of the appliance.

As before, a trans-palatal bar 87 connects the right and left posterior appliance segments together, allowing for the sake of simplicity and ease of use by the patient, the posterior appliance segment to be held together in one piece. It also is helpful for the sake of posterior tooth control, to prevent tipping and rotation, and to control arch width, if the posterior teeth are held together as a unit. In this case, a Nance holding arch is not used, although which type of trans-palatal connector is used or not used is up to the individual doctor treating the case. These appliance features can be combined in a customized series of appliances to provide ideal individualized treatment for many types of malocclusion problems.

Figure 9:
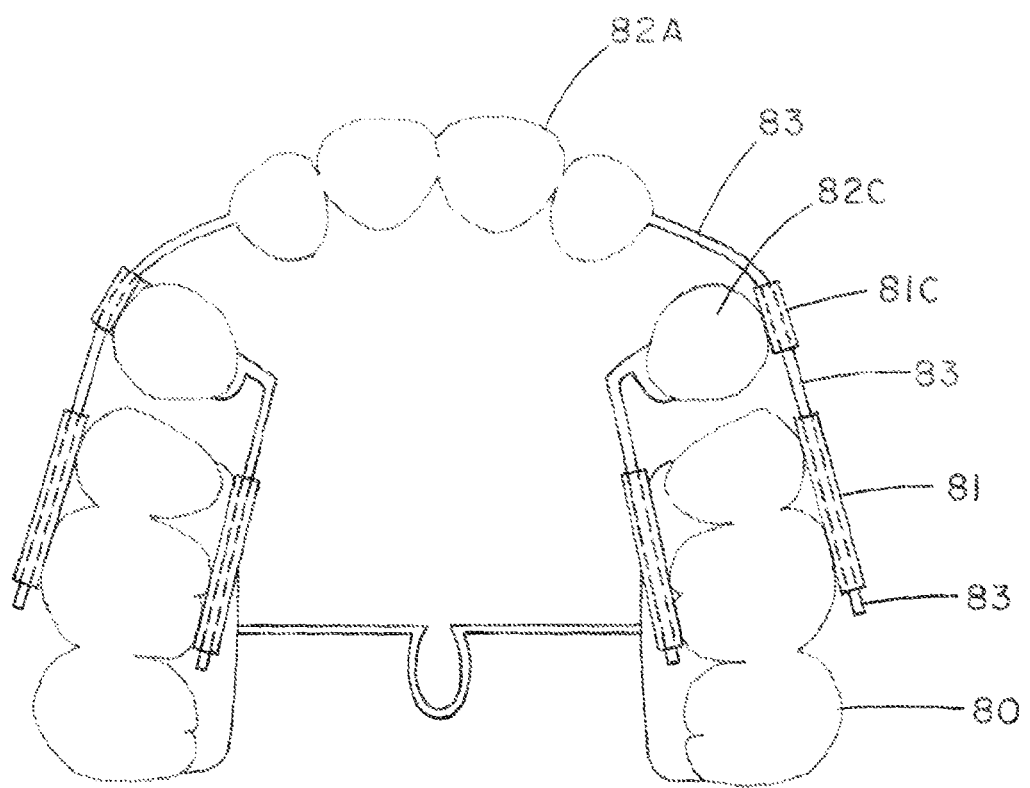
FIG. 9 shows an occlusal view of another appliance similar to that shown in FIG. 8 with a single anterior appliance segment covering the four incisors.

FIG. 9 is an occlusal view of another appliance similar to that shown in FIG. 8. This appliance is intended primarily for use at a later stage of treatment after the appliance shown in FIG. 8. This appliance, when disassembled by the patient outside of the mouth for cleaning purposes, is composed of four segments. The posterior segment of this appliance is the same as that shown in FIG. 8. As in FIG. 8, there are tooth-clasping elements 82C covering the cuspid teeth. The difference between this FIG. 9 and FIG. 8 is that there is a single anterior appliance segment 82A covering the four incisors, and there are sliding tabs 83 extending from the anterior segment through flat buccal tubes 81C on the cuspid elements. This embodiment is very similar to that shown in FIG. 1, except in this embodiment there are buccal and lingual sliding tabs 83. The sliding tabs on the lingual side of the teeth are attached to the tooth-clasping elements 82C covering the cuspids as in FIG. 8. This embodiment differs from FIG. 8 in that the buccal side sliding tab 83 originates from, and is attached to the anterior appliance segment 82A. The buccal sliding tab 83 passes through a flat buccal tube 81C on its way back to the posterior segment where it slides through a second flat buccal tube 81 in just the same manner as is shown in FIGS. 1 and 8. Not shown in the occlusal views are the stretchable elastic elements 86 which provide the force for space closure that are shown in FIGS. 1 and 2. These elastic elements 86 typically require hooks 84 and 85 or other types attachment points so they can be removably attached.

In the case of the appliance shown in FIG. 9, force is required to continue to retract the cuspid teeth, which are shown partially retracted in this drawing, and additional force is required to retract the four incisor teeth covered by the anterior appliance segment 82A. It is therefore anticipated that two elastic elements will be required on each side simultaneously if it is desired by the orthodontist to retract cuspids and incisors simultaneously. Obviously, enough hooks would need to be present to allow the attachment of four elastics at one time. There are treatment situations where it is considered undesirable to avoid causing anterior molar slippage, or anchorage loss, and in those situations it would be best to retract cuspids first, and then to retract incisors. In this embodiment of the present appliance, the buccal sliding tabs 83 originate from and are an integral formed part of the anterior appliance segment 82A. In this case, the lingual sliding tabs originate from, and are an integrally-formed part of the cuspid tooth-clasping elements 82C.

Figure 10:
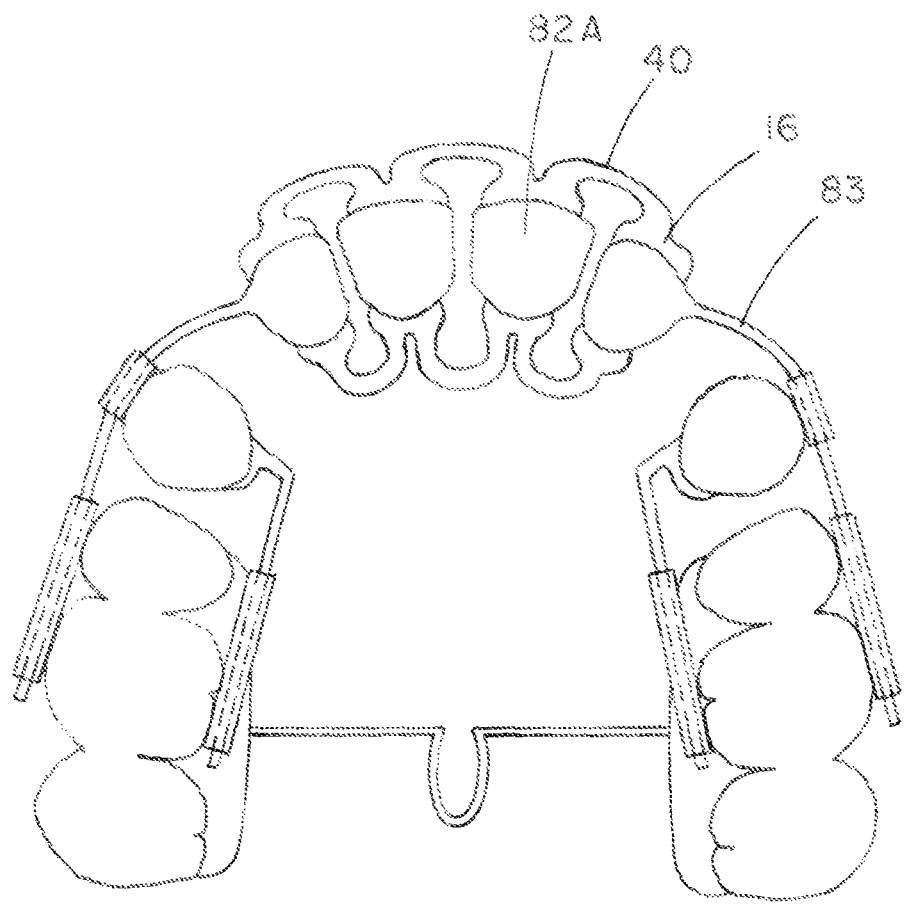
FIG. 10 presents an occlusal view of another appliance similar to that shown in FIG. 9, in which the anterior segment has separate tooth-clasping elements for each of the four incisor teeth with curved interconnecting elements 40 on both the facial and lingual sides.

FIG. 10 is an occlusal view of another appliance, similar to the one shown in FIG. 9, and also made in four separate segments as in FIG. 9 that can be disassembled for cleaning purposes. The posterior appliance segment covering the posterior teeth left and right for anchorage, and connected with a trans-palatal bar is exactly the same as in FIG. 9. The two cuspid tooth-clasping elements with their attached lingual sliding tabs and with their flat buccal tubes to receive and pass through the sliding tabs from the anterior segment are also the same as the one shown in FIG. 9. The difference here is the tooth-clasping elements for the incisors are all individual elements for each of the four incisor teeth 82A, connected by flexible interconnecting loops 40 on both the buccal and lingual aspects.

The entire anterior appliance segment can be a single piece of clear plastic material, integrally formed with the sliding tabs 83 that extend posteriorly as in FIG. 9 through the flat tubes 81C on the cuspid tooth-clasping elements back toward and through the second flat buccal tubes 81 on the posterior appliance segment. For purposes of illustration, only the flanges 16 and the facial side flexible interconnecting loops are shown in this drawing. However, it must be understood that because of the normal angulation of the incisor teeth they would not be visible from a straight-on occlusal view. These features therefore are diagrammatic in this figure and not realistic. It also is to be understood that we have utilized this particular embodiment to illustrate the possibility of aligning incisor teeth in an extraction case simultaneous with cuspid retraction when other embodiments of the present appliance might also be just as easily workable for incisor alignment, such as embodiments employing metal wire interconnecting elements, or short flexible interconnecting elements made of some other material, etc. If those embodiments are utilized for the purpose of aligning incisors, then obviously the anterior segment would not be made of a single piece of clear flexible material.

Figure 11:
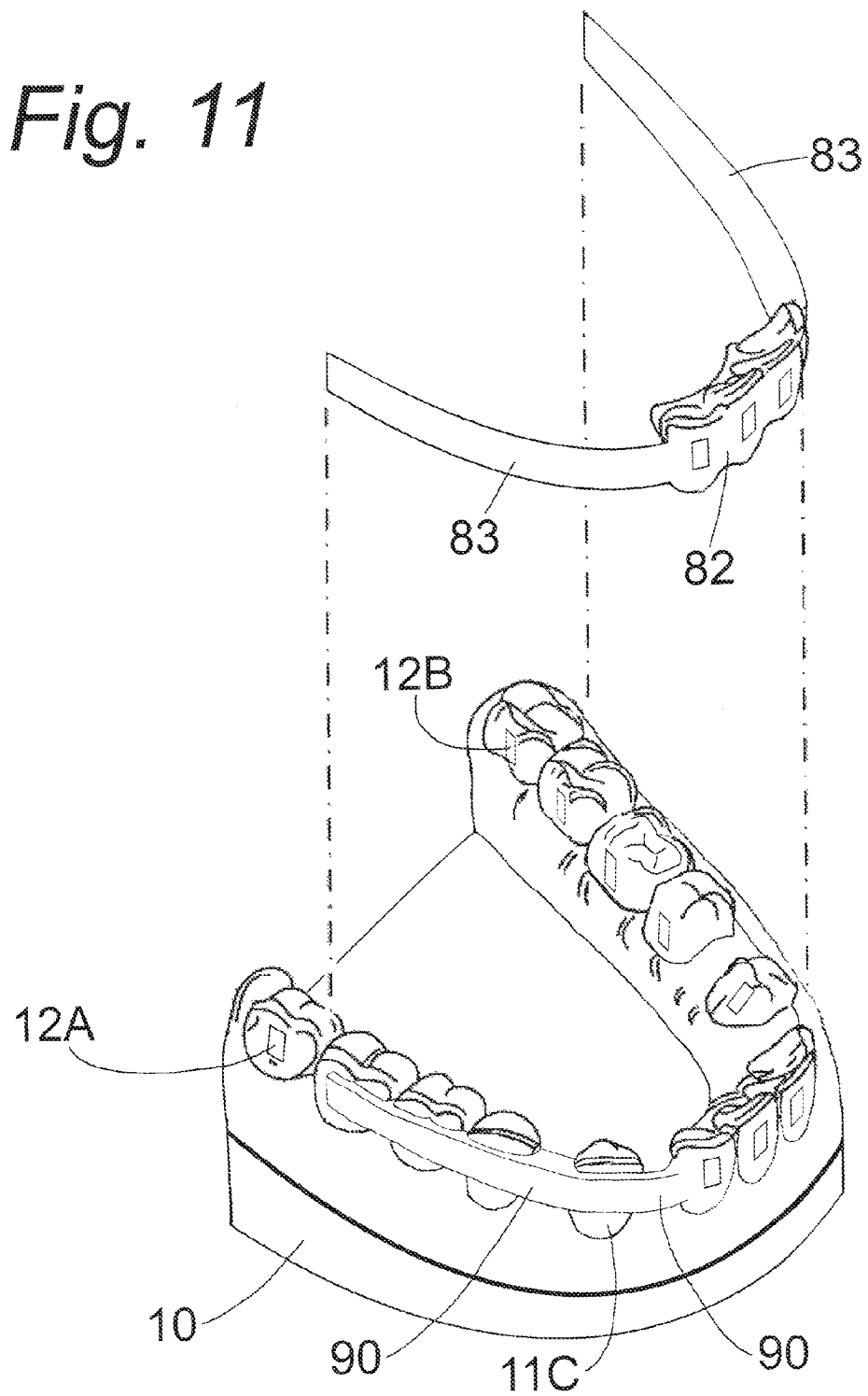
FIG. 11 is a perspective view of a model of a patient's teeth (below) with forming guides added to the posterior teeth for the fabrication of sliding tabs attached to the anterior appliance segment. Directly above the tooth model is an embodiment of the anterior appliance segment that has been thermoformed over the model, showing the sliding tabs.

FIG. 11 is a perspective view of a dental model with the left and right first premolar teeth removed. The model base 10 is shown. The left and right cuspid teeth 11 have drifted back away from the four incisor teeth which are all together in this case. Rectangular bonded attachments are attached on the buccal side 12A of most of the teeth and rectangular bonded attachments are also attached on the lingual side of each tooth, although not all of them are visible in this view. A forming guide 90 is applied to the facial surfaces of the cuspids and the posterior teeth, blending smoothly into the shape of the lateral incisor at the anterior end. The lateral surface of the forming guide is smoothly curved along the facial surfaces of the teeth to serve as a mold for the fabrication of a thermoformed sliding tab extending posteriorly from the anterior appliance segment which will be thermoformed over the four incisor teeth. Above the dental model is a completed anterior appliance segment 82 with its two sliding tabs 83 that has been thermoformed over the model. The excess material of the flat clear sheet of thermoplastic material from which the appliance segment was made by thermoforming has been trimmed away leaving the completed anterior appliance segment.

Figure 12:
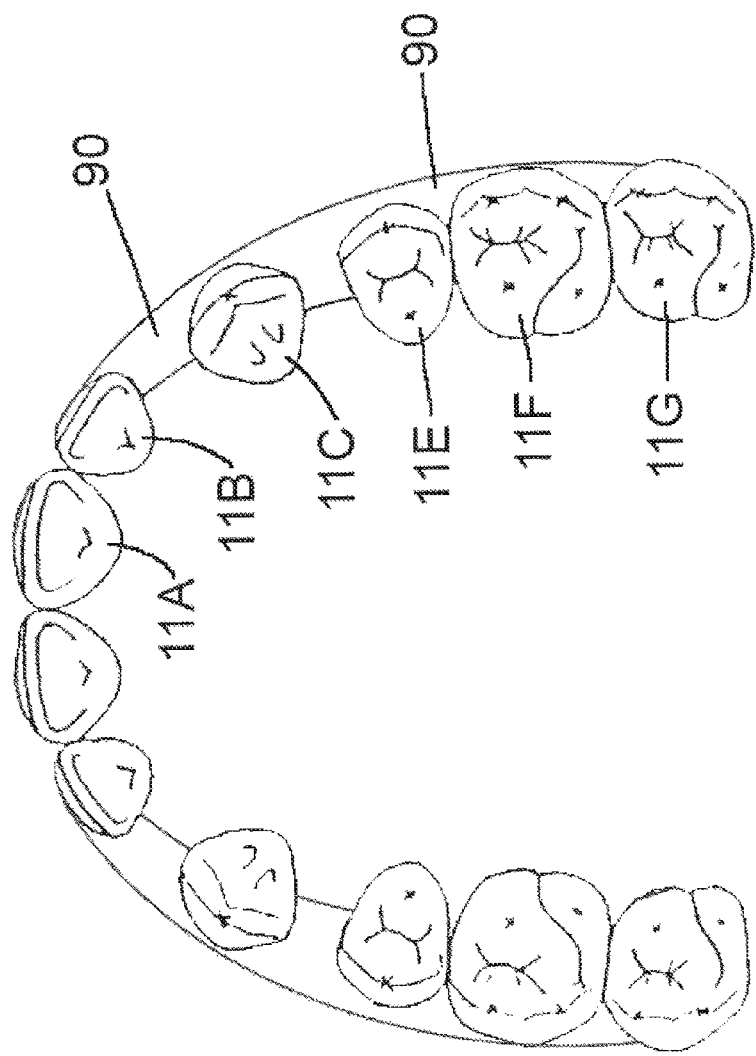
FIG. 12 is an occlusal view of a tooth model with forming guides applied to the posterior teeth for the fabrication of sliding tabs.

FIG. 12 shows an occlusal view of a dental model with the first premolars, left and right, removed as in FIG. 11. The base of the model is not shown in this figure. The teeth are numbered as in the other drawings shown in this disclosure. The central incisor is 11A. The lateral incisor is 11B. All four incisor teeth are together. The cuspid teeth 11C are moved posteriorly from their normal location about half-way back toward their eventual final position against the second premolar 11E as they would be in a partially treated extraction case. The first molar tooth 11F and the second molar tooth 11G are in their normal position. Curving smoothly along the facial surfaces of the teeth from the lateral incisor is a forming guide for the fabrication of a sliding tab, similar to the one shown in FIG. 11. Although this guide could be formed on a plaster model manually, it would require much time to produce. It is anticipated that for most applications this forming guide would be generated in a computer by modifying a digital data set of a surface scan of a dental model. A new dental model with the forming guide could then be produced by using a 3-D printer or by using a CNC milling machine.

Figure 13:
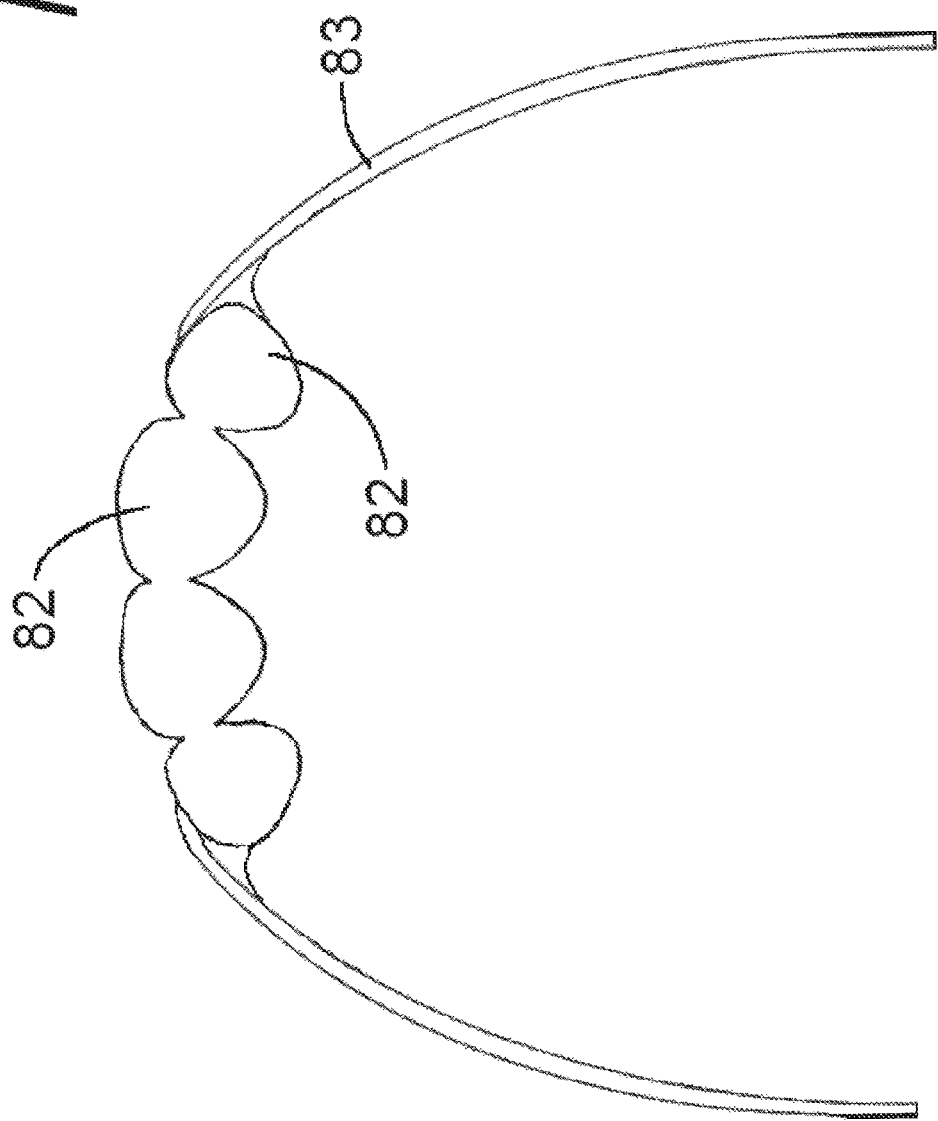
FIG. 13 is an occlusal view of an anterior appliance segment with sliding tabs extending posteriorly.

FIG. 13 is an occlusal view of the anterior segment 82 of an extraction space closing appliance with the curved sliding tabs 83 extending posteriorly on each side. In this figure, it is anticipated that this appliance segment will be thermoformed over the dental model with the forming guides as is shown in FIGS. 11 and 12. The anterior appliance segment covers the four incisor teeth.

Figure 14:
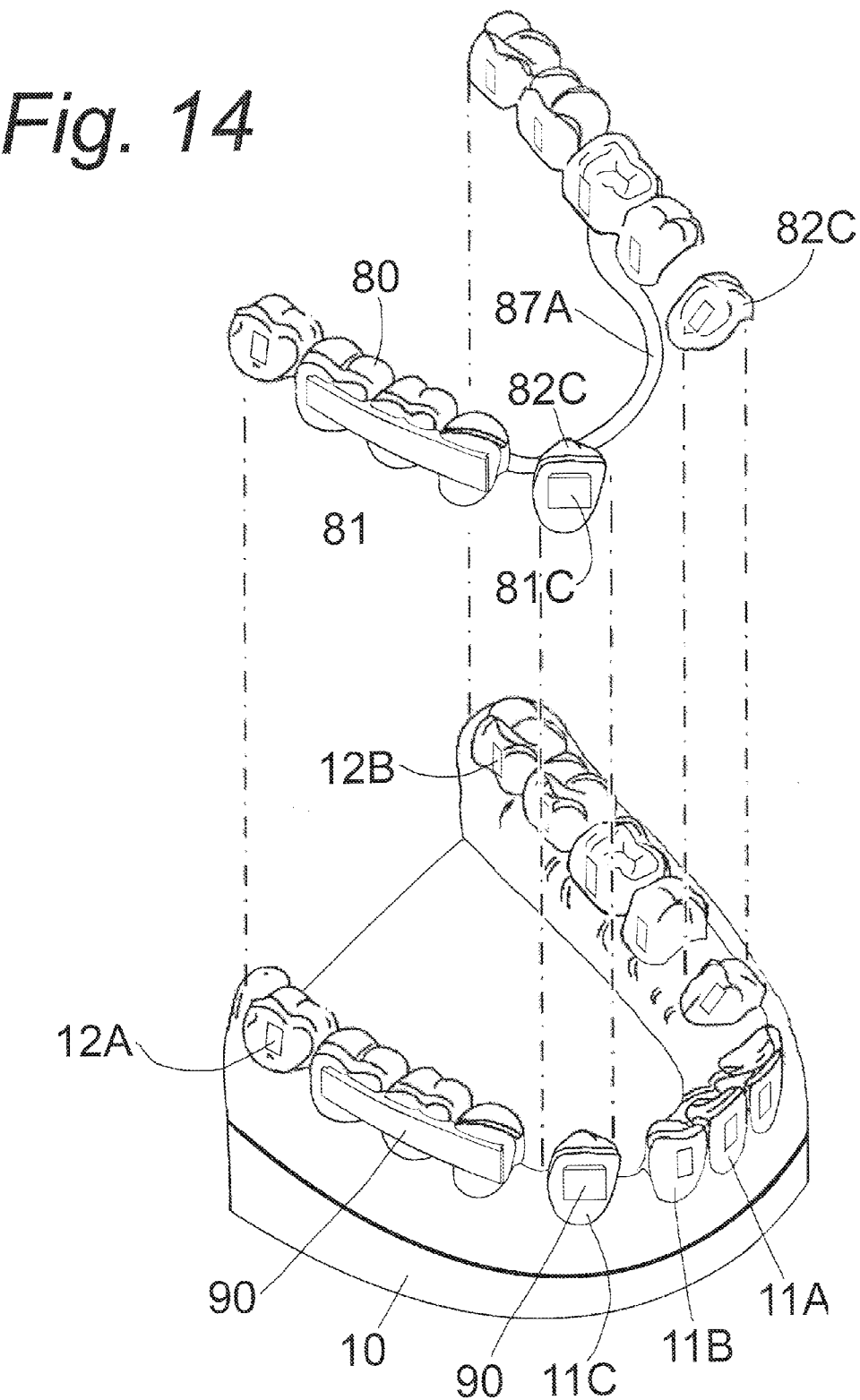
FIG. 14 is a perspective view of a tooth model (below) with long forming guides applied to the posterior teeth for the fabrication of flat tubular receptacles. Shorter guides are applied to the cuspid teeth. Positioned directly above the model are appliance segments. The posterior right and left segments are joined by a lingual bar. The cuspid teeth have individual tooth clasping elements, which are separate appliance segments, left and right.

FIG. 14 shows a dental model (below) where the left and right first premolar teeth have been extracted. The base of the model 10 is shown. The cuspid teeth 11C have been partially retracted away from the four incisor teeth (right side teeth 11A and 11B are labeled) as would be expected in a partially treated extraction case. Bonded rectangular attachments are shown on the facial side of the teeth 12A and lingual side of the teeth 12B. Forming guides 90 are shown on the facial side of the posterior teeth so that formed receptacles for receiving the sliding tabs can be fabricated. A shorter forming guide (also labeled 90) on the facial side of the cuspid tooth is also shown. Above the dental model are shown the posterior extraction appliance segments left and right (right side labeled 80) connected together by a lingual bar. The formed receptacle 81 in the shape of a flat tube to receive the sliding tab (not shown in this drawing) is positioned on the facial side of the posterior teeth. Separate cuspid tooth clasping elements (labeled on the right and left sides 82C) are shown, which are appliance segments for retracting the cuspids. The formed receptacle to receive the sliding tab for this segment on the right side is labeled 81C.

Figure 15:
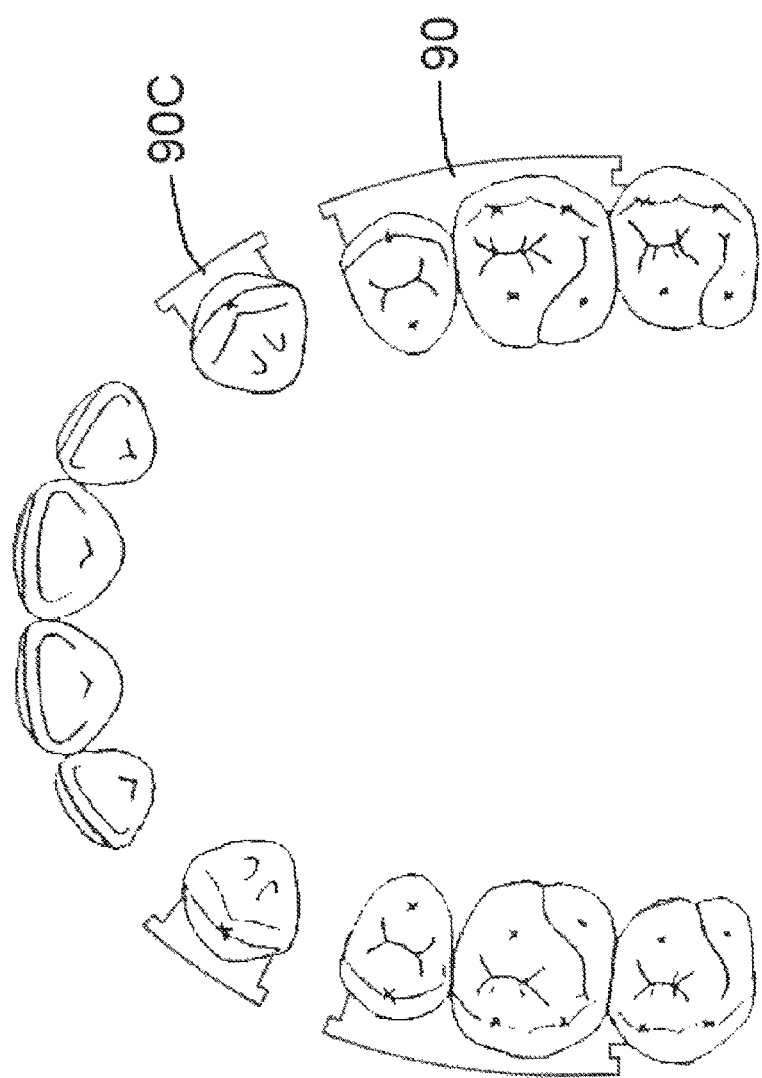
FIG. 15 is an occlusal view of a model with forming guides applied to the posterior teeth for the fabrication of receptacles to receive sliding tabs.

FIG. 15 is an occlusal view of a model of upper teeth. The two first premolar teeth have been extracted. The cuspid teeth, right and left, are partially retracted away from their normal position against the lateral incisors toward their eventual new position against the second premolars, as they would be in a partially treated extraction case. Forming guides 90 have been applied to the facial surfaces of the posterior teeth and 90C to the facial surfaces of the cuspid teeth. Note that the facial side of the forming guides follows a smooth curve, roughly corresponding to the facial side of the teeth. Each forming guide includes a small projection on both the mesial and distal surfaces. After appliance segments are thermoformed over the model, it is planned for the clear material to be trimmed to remove the projection, leaving an open thin slot just the right dimension for insertion of the thin flat sliding tab which is a part of the anterior segment in this extraction appliance.

Figure 16:
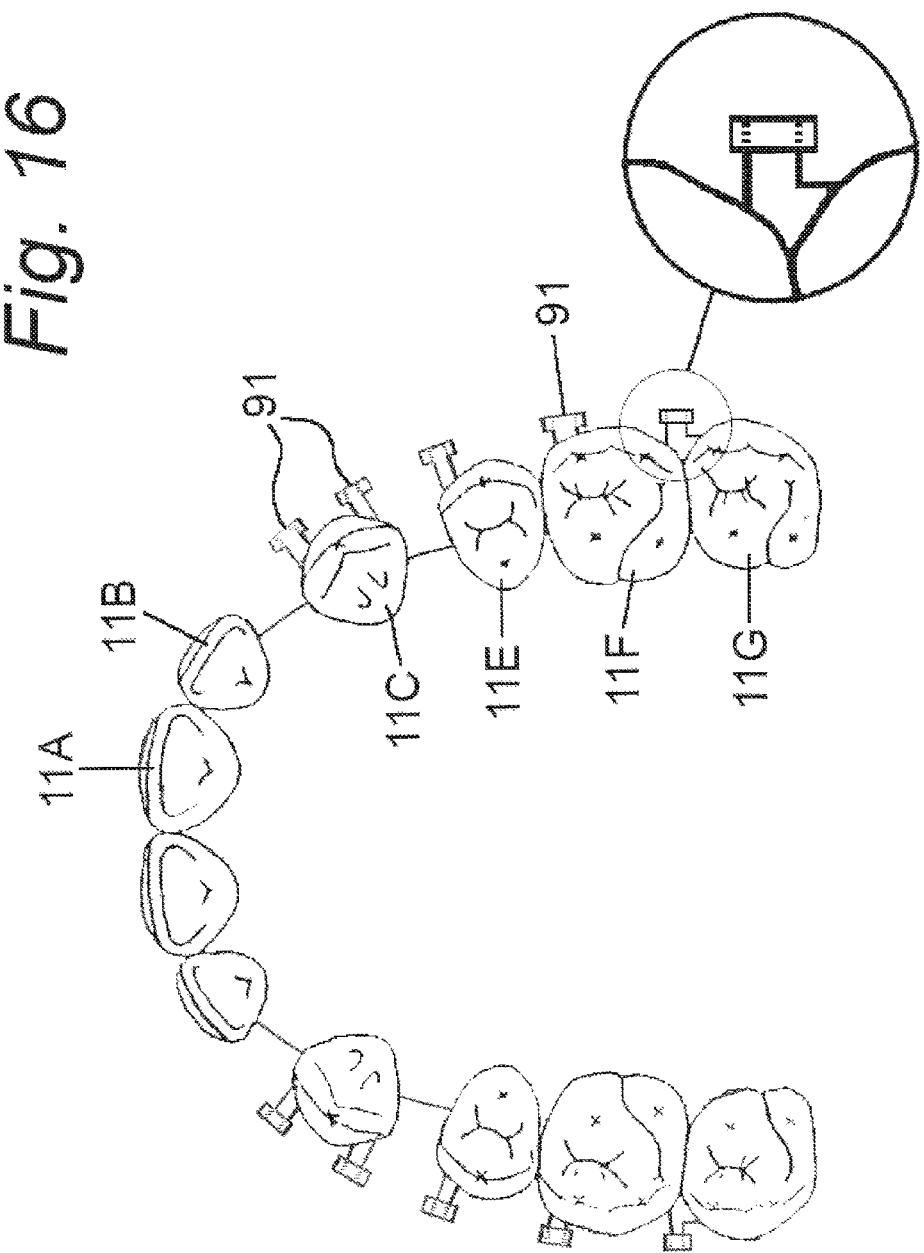
FIG. 16 is an occlusal view of a tooth model showing another variation with short forming guides on the buccal surfaces of the posterior teeth for the fabrication of short receptacles to receive sliding tabs from the anterior appliance segment.

FIG. 16 is also an occlusal view of a model of upper teeth very much like FIG. 15. Again, the two first premolar teeth have been extracted. The cuspid teeth, right and left, are partially retracted away from their normal position against the lateral incisors toward their eventual new position against the second premolars, as they would be in a partially treated extraction case. This drawing illustrates short forming guides 91 which have been applied to the facial surfaces of the cuspid teeth 11C, and also to the posterior teeth 11E, 11F, and 11G. Note that the forming guides 91 are not placed in the center of the teeth to allow the placement of bonded attachments (not shown in this drawing, but shown in most of the other drawings). Each short forming guide includes a small projection on both the mesial and distal surfaces. It is planned that these projections will be cut away along the dotted lines to leave a thin vertically oriented opening of just the right size to allow insertion of the sliding tab from the anterior appliance segment. Notice the location of the forming guides follows the same smooth curve along the buccal surfaces of the teeth to correspond to the shape of the sliding tab, so the tab will be able to slide freely and allow the teeth to have the ideal arch form. A close-up magnified view of the forming guide between the first molar 11F and the second molar 11G is shown.

Figure 17:
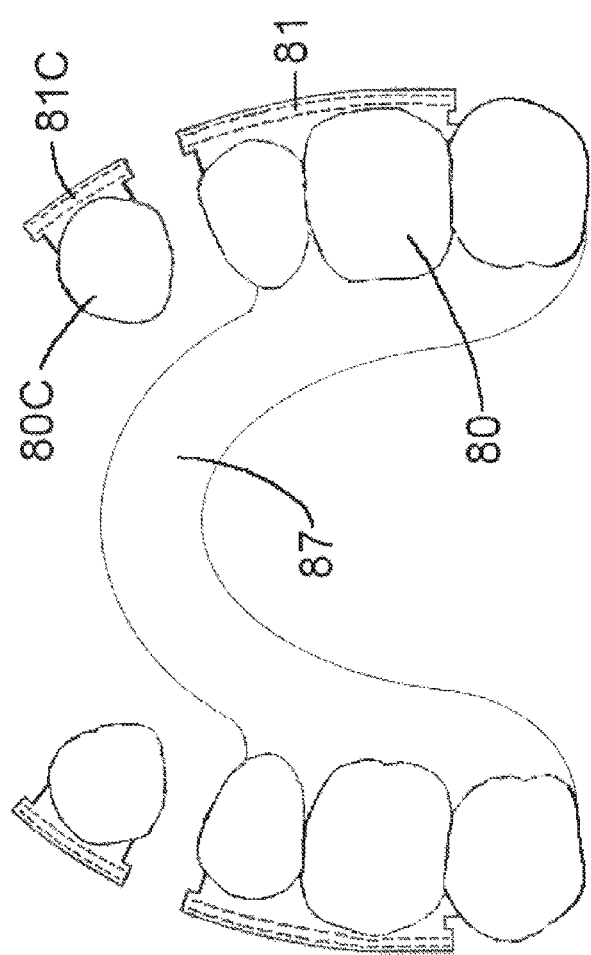
FIG. 17 is an occlusal view of a posterior appliance segment after it has been thermoformed over a tooth model with long forming guides applied for the production of receptacles. Also shown are single tooth appliance segments to fit over the right and left cuspid teeth.

FIG. 17 is an occlusal view of a finished posterior segment of a space closing appliance that has been thermoformed over a model such as the one shown in FIG. 15. The posterior appliance segment 80 includes coverage of the second premolar, the first molar, and the second molar. Note that the left and right posterior segments are in this case joined together by a connector element 87. This connector element can be a thin bar as shown here made of the same material as the thermoformed tooth clasping elements. It can be wider and cover more of the palate, or it can be any reasonable shape, such as a connector with a Nance button as shown in FIG. 7. The connector can alternatively be made of some other suitable material, such as a metal wire formed in the shape of a trans-palatal bar. There are many acceptable materials and shape combinations. Again, note that in this drawing no bonded attachments are shown, but it is anticipated that bonded attachments will be placed on several teeth, especially those nearest the extraction sites. A rectangular bonded attachment would help prevent tipping of the teeth as the spaces are closed. The placement and shape of the bonded attachments, as stated earlier, can vary. The formed receptacles 81 and 81C correspond in shape to the long forming guides shown in FIG. 15. The dotted lines in this case refer to the path that the sliding tab will take inside the hollow space within the formed receptacles. The projections on the mesial and distal ends of the receptacles will be trimmed away to make a vertical slot opening into which the sliding tabs will be inserted, but the projections have not yet been trimmed away in this drawing.

Figure 18:
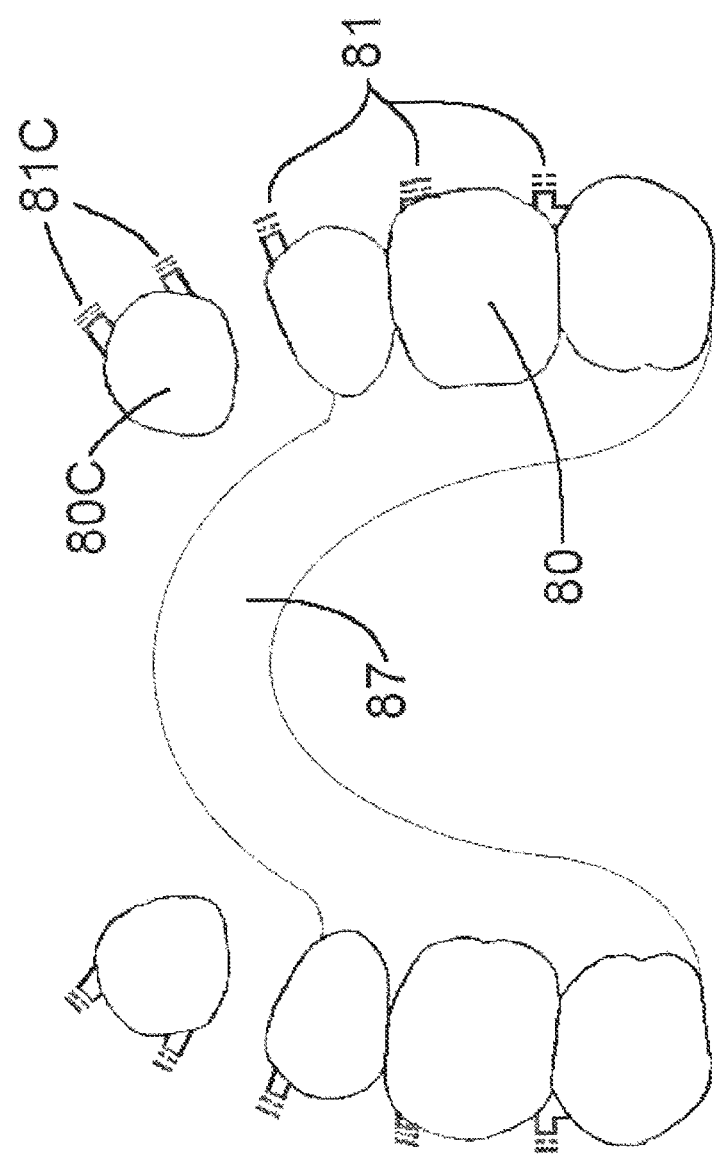
FIG. 18 is an occlusal view of a posterior appliance segment after it has been thermoformed over a tooth model with short forming guides applied for the production of receptacles. Also shown are single tooth appliance segments to fit over the right and left cuspid teeth.

FIG. 18 is an occlusal view of the finished posterior segments of a space closing appliance with short forming guides. The appliance segment 80 was thermoformed over a model similar to that shown in FIG. 16. It would be impossible to remove the formed appliance from the model without first removing the projections on the mesial and distal of each forming guide because the appliance would be "locked on" to the model by undercuts. By removing the projections on the formed receptacles, an open slot will be produced on the receptacles which will allow them to receive the sliding tabs from the anterior appliance segment. Note that there is an individual tooth clasping appliance segment 80C for each of the cuspid teeth, left and right.

Figure 19:
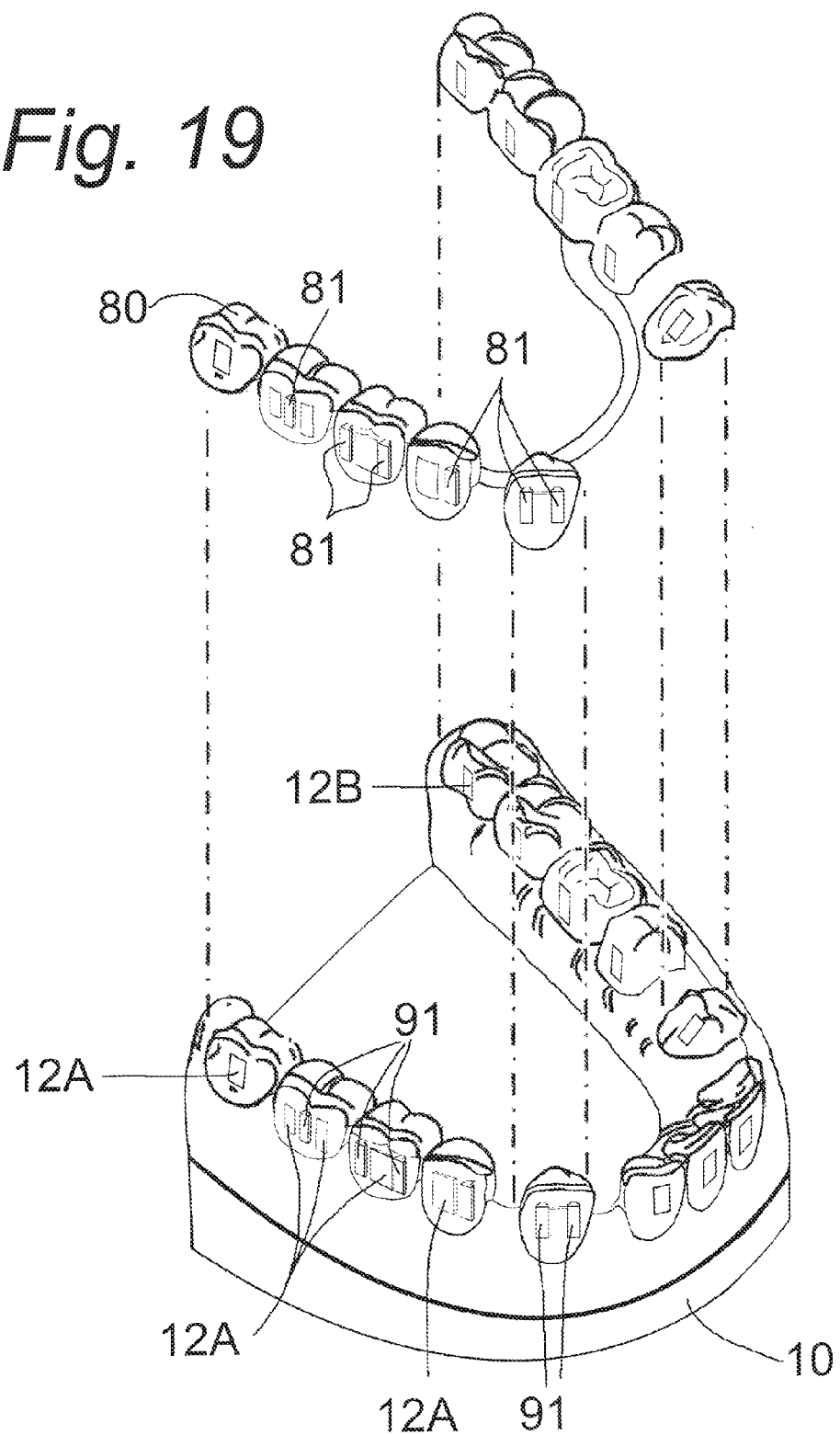
FIG. 19 is a perspective view of a tooth model (below) with multiple short forming guides applied to posterior teeth for the fabrication of flat tubular receptacles. A thermoformed appliance made to fit the model is positioned directly above the model.

FIG. 19 is a perspective view of a dental model (below) with both first premolar teeth removed. The base 10 of the model is shown. Rectangular bonded attachments 12A on the facial side of the teeth can be seen. Short forming guides 91 for the fabrication of short receptacles are positioned close to the bonded attachments. Positioned above the dental model is the posterior segment of a space closure appliance 80. Multiple formed short receptacles 81 to receive the sliding tabs are visible on the facial side of the appliance segment. The two posterior segments covering the molars and second premolars are joined together by a lingual connector element that can be made of any suitable material. This appliance is very similar to the appliance shown in FIG. 18. There are differences in the number of forming guides shown on the posterior teeth, but otherwise the dental models are similar.

Figure 20:
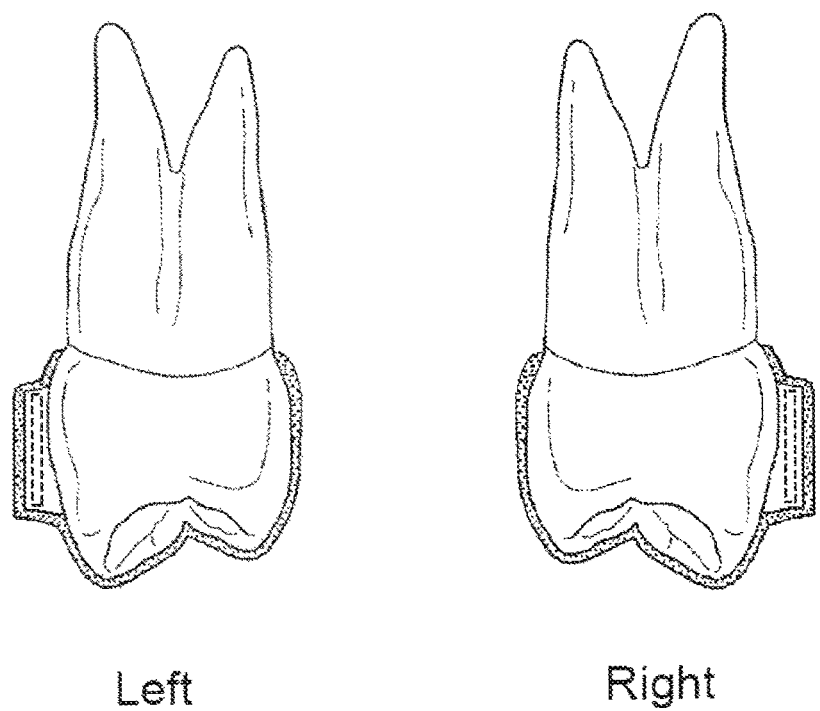
FIG. 20 is an antero-posterior view of left and right upper premolar teeth with appliance segments fitted over them showing the formed receptacles for receiving the sliding tabs from the anterior appliance segment.

FIG. 20 is an antero-posterior view of two premolars with a thermoformed appliance segment in place covering the buccal, occlusal and lingual surfaces. There is a formed receptacle on the buccal surface that was produced by forming the plastic material over a forming guide. This is a cross-section taken through the center of a receptacle. The dashed lines on the interior of the receptacle indicate where the sliding tab will pass through as this removable appliance works to close the interdental space.

Figure 21:
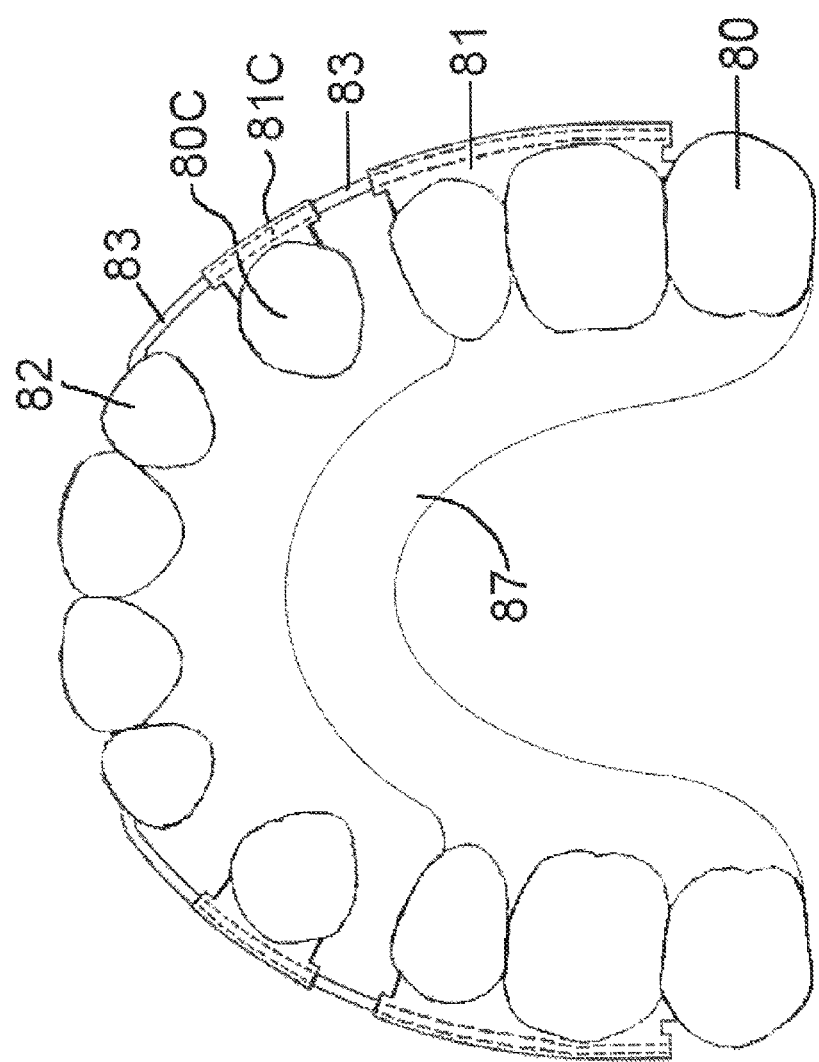
FIG. 21 is an occlusal view of an assembled space closing appliance with the anterior appliance segment containing the sliding tabs and the posterior appliance segments with buccal receptacles in place to receive the sliding tabs.

FIG. 21 is an occlusal view of an assembled space closing appliance. This particular embodiment is composed of four different segments: The anterior segment 82 covers the four incisors and also includes the sliding tabs 83 that extend posteriorly from the lateral incisors, where the tabs smoothly blend into the contour of the lateral incisor tooth clasping element. The next two segments 80C, bilaterally cover only the cuspid teeth. The posterior segment is composed of two tooth clasping elements covering the second premolars and also both the first and second molars, one three-tooth segment 80 on each side. Each of these three-tooth segments is connected together across the midline by a connector 87. The sliding tabs 83 pass through flat tubes (receptacles 81C on the cuspid segments, and 81 on the posterior segment) on the facial side. The dashed lines indicate the location of the sliding tabs as they pass through the receptacles. It is also possible to fabricate this appliance in much the same way as was shown in FIG. 9, with facial side and also lingual side sliding tabs.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. A tooth-positioning appliance comprising:
    bonded attachments bonded to protrude from selected teeth;
    a first appliance segment having:
    (a) a thin shell with recesses for removably engaging a first set of teeth;
    (b) tooth-clasping elements on the thin shell of the first appliance segment for removably engaging the bonded attachments on the first set of teeth; and
    (c) a flat receptacle extending horizontally on the thin shell of the first appliance segment;
    a second appliance segment having:
    (a) a thin shell with recesses for removably engaging a second set of teeth, wherein the first set of teeth and the second set of teeth are separated by a space;
    (b) tooth-clasping elements on the thin shell of the second appliance segment for removably engaging the bonded attachments on the second set of teeth; and
    (c) a thin elongated tab extending laterally from the second appliance segment spanning the space and in sliding engagement with the flat receptacle of the first appliance segment, the thin shell and thin elongated tab of the second appliance segment being a single piece of material; and
    an activating element connected between the first appliance segment and the second appliance segment exerting a force to change the size of the space as the tab slides with respect to the flat receptacle.

2. The tooth-positioning appliance of claim 1 wherein at least one of the tooth clasping elements comprise a hole in the thin shell for receiving and engaging a bonded attachment protruding from a tooth.

3. The tooth-positioning appliance of claim 1 wherein at least one of the tooth clasping elements comprise a recess in the thin shell for receiving and engaging a bonded attachment protruding from a tooth.

4. The tooth-positioning appliance of claim 1 wherein the first appliance segment further comprises:
    a left posterior appliance segment removably engaging selected left posterior teeth and having a flat receptacle;

a right posterior appliance segment removably engaging selected right posterior teeth and having a flat receptacle; and a trans-palatal bar extending between the left posterior appliance segment and the right posterior appliance segment;

and wherein the second appliance segment removably engages selected anterior teeth, with thin elongated tabs extending laterally in sliding engagement with the flat receptacles on the left posterior appliance segment and right posterior appliance segment.

5. The tooth-positioning appliance of claim 1 wherein the tab is a vertical ribbon allowing flexibility in the horizontal plane.

6. The tooth-positioning appliance of claim 1 wherein the flat receptacle extends horizontally on the buccal aspect of the thin shell of the first appliance segment.

7. The tooth-positioning appliance of claim 1 wherein the flat receptacle extends horizontally on the lingual aspect of the thin shell of the first appliance segment.

8. A tooth-positioning appliance comprising:
a first appliance segment having:
(a) a thin shell with recesses for removably engaging a first set of teeth; and
(b) a vertical slot extending horizontally on the thin shell of the first appliance segment;
a second appliance segment having:
(a) a thin shell with recesses for removably engaging a second set of teeth, wherein the first set of teeth and the second set of teeth are separated by a space; and
(b) a thin flexible elongated tab extending laterally in a vertical orientation from the second appliance segment spanning the space and in sliding engagement with the vertical slot of the first appliance segment, the thin shell and thin flexible elongated tab of the second appliance segment being a single piece of material; and
an activating element connected between the first appliance segment and the second appliance segment exerting a force to change the size of the space as the tab slides with respect to the vertical slot, wherein the tab and vertical slot allow relative movement in the horizontal plane between the first appliance segment and the second appliance segment.

9. The tooth-positioning appliance of claim 8 wherein the tab is a vertical ribbon allowing flexibility in the horizontal plane.

10. The tooth-positioning appliance of claim 8 wherein the vertical slot extends horizontally on the buccal aspect of the thin shell of the first appliance segment.

11. The tooth-positioning appliance of claim 8 wherein the vertical slot extends horizontally on the lingual aspect of the thin shell of the first appliance segment.

12. A tooth-positioning appliance comprising:
bonded attachments bonded to protrude from selected teeth;
an anterior appliance segment having:
(a) a thin shell with recesses for removably engaging a set of anterior teeth, wherein the set of anterior teeth and at least one set of posterior teeth are separated by at least one space;
(b) tooth-clasping elements on the thin shell of the anterior appliance segment for removably engaging the bonded attachments on the set of anterior teeth; and
(c) at least one thin elongated tab extending laterally from the anterior appliance segment spanning the space, the thin shell and the at least one thin elongated tab of the anterior appliance segment being a single piece of material.

13. The tooth-positioning appliance of claim 12 wherein the at least one thin elongated tab is a vertical ribbon allowing flexibility in the horizontal plane.

14. The tooth-positioning appliance of claim 12, further comprising:
a right posterior appliance segment having:
(a) a thin shell with recesses for removably engaging a set of right posterior teeth that are separated from the set of anterior teeth by a first space of the at least one space;
(b) tooth-clasping elements on the thin shell of the right posterior appliance segment for removably engaging the bonded attachments on the set of right teeth; and
(c) a flat receptacle extending horizontally on the thin shell of the right posterior appliance segment, the flat receptacle being in sliding engagement with a first tab of the at least one thin elongated tab of the anterior appliance segment;
a left posterior appliance segment having:
(a) a thin shell with recesses for removably engaging a set of left posterior teeth that are separated from the set of anterior teeth by a second space of the at least one space;
(b) tooth-clasping elements on the thin shell of the left posterior appliance segment for removably engaging the bonded attachments on the set of left teeth; and
(c) a flat receptacle extending horizontally on the thin shell of the right posterior appliance segment, the flat receptacle being in sliding engagement with a second tab of the at least one thin elongated tab of the anterior appliance segment;
a trans-palatal bar extending between the left posterior appliance segment and the right posterior appliance segment; and
activating elements connected between the anterior appliance segment and the posterior appliance segments exerting a force to change the size of the first space and the second space as the tabs slide with respect to the flat receptacles.

15. The tooth-positioning appliance of claim 14 wherein the flat receptacles extend horizontally on the buccal aspect of the thin shells of the posterior appliance segments.

16. The tooth-positioning appliance of claim 14 wherein the flat receptacles extend horizontally on the lingual aspect of the thin shells of the posterior appliance segments.

* * * * *